(12) United States Patent
Burn et al.

(10) Patent No.: US 12,181,411 B2
(45) Date of Patent: Dec. 31, 2024

(54) DETECTION METHOD

(71) Applicant: THE UNIVERSITY OF QUEENSLAND, St Lucia (AU)

(72) Inventors: Paul Leslie Burn, Kenmore (AU); Paul Edward Shaw, Chelmer (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 0 days.

(21) Appl. No.: 17/940,276

(22) Filed: Sep. 8, 2022

(65) Prior Publication Data

US 2023/0039657 A1    Feb. 9, 2023

Related U.S. Application Data

(63) Continuation of application No. 16/759,533, filed as application No. PCT/AU2018/051157 on Oct. 26, 2018, now abandoned.

(30) Foreign Application Priority Data

Oct. 26, 2017  (AU) ................................ 2017904338
Aug. 23, 2018  (AU) ................................ 2018903104

(51) Int. Cl.
| | | |
|---|---|---|
| G01N 21/64 | (2006.01) | |
| C07D 285/14 | (2006.01) | |
| C09K 11/06 | (2006.01) | |
| G01N 21/85 | (2006.01) | |

(52) U.S. Cl.
CPC ....... *G01N 21/6428* (2013.01); *C07D 285/14* (2013.01); *C09K 11/06* (2013.01); *G01N 21/85* (2013.01); *C09K 2211/1018* (2013.01); *G01N 2021/6432* (2013.01); *G01N 2021/8578* (2013.01)

(58) Field of Classification Search
CPC .. G01N 21/6428; G01N 21/85; C07D 285/14; C09K 11/06
See application file for complete search history.

(56) References Cited

U.S. PATENT DOCUMENTS

| | | | |
|---|---|---|---|
| 5,155,046 A * | 10/1992 | Hui ..................... | G01N 21/7703 422/82.07 |
| 7,812,323 B2 | 10/2010 | Burn et al. | |
| 10,234,390 B2 * | 3/2019 | Voelcker ............... | G01N 33/553 |
| 2006/0194218 A1 * | 8/2006 | Cook .................. | C12Q 1/6897 534/727 |
| 2016/0018371 A1 * | 1/2016 | Acharya ............ | G01N 33/0037 436/121 |
| 2018/0356405 A1 * | 12/2018 | Chou .................. | G01N 21/6452 |
| 2020/0354356 A1 * | 11/2020 | Zang ..................... | G01N 27/126 |

* cited by examiner

*Primary Examiner* — Hugh Maupin
(74) *Attorney, Agent, or Firm* — Nixon & Vanderhye P.C.

(57) ABSTRACT

The present invention relates to an optical sensing element for detection of a narcotic, the optical sensing element comprising a fluorescent sensing compound provided on a substrate, wherein emission of the fluorescent sensing compound is quenched in the presence of the narcotic, and wherein the fluorescent sensing compound is non-polymeric and comprises an electron donor moiety, an electron acceptor moiety and a moiety that influences solubility of the compound in a solvent. Sensing devices incorporating the sensing element and methods of detecting narcotics are also described.

19 Claims, 13 Drawing Sheets

DETECTION METHOD

CROSS-REFERENCE TO RELATED APPLICATIONS

Figure 1:
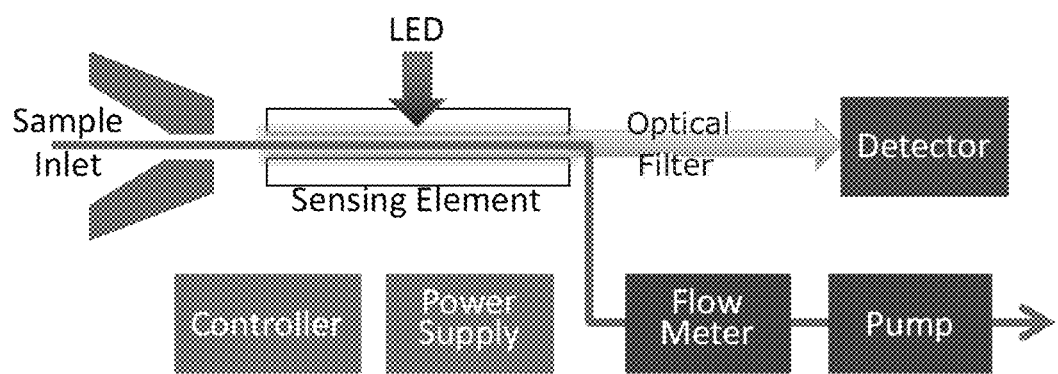

This application is a continuation of U.S. patent application Ser. No. 16/759,533 filed 27 Apr. 2020, which is the U.S. national phase of International Application No. PCT/AU2018/051157 filed 26 Oct. 2018, which claims priority from Australian Provisional Application No. 2017904338 entitled "Detection Method" filed 26 Oct. 2017 and from Australian Provisional Application No. 2018903104 entitled "Narcotics Detection" filed 23 Aug. 2018, the contents of which are hereby incorporated herein by reference.

FIELD OF THE INVENTION

The present invention relates to the detection of narcotics. In particular, the present invention relates to an optical sensing element used for the detection of narcotics, to a sensing device incorporating the sensing element and to a method of detecting narcotics based on the properties of the optical sensing element.

BACKGROUND TO THE INVENTION

There is an on-going need to develop techniques that allow detection of narcotics. It is important that detection is suitably sensitive and selective.

Various detection methods for narcotics are currently available. Colourimetric-based methods rely on a chemical reaction taking place between an analyte (narcotic) and sensing compound to give a coloured response that is indicative of the analyte being present. The relevant reaction is solution-based and this methodology has not been demonstrated as applicable for detection of narcotics in the vapour phase.

A variety of other methods for detecting narcotics have been developed involving analytical techniques such as thin-layer chromatography, mass spectrometry, high performance liquid chromatography and immunoassay methodologies. However, these methods are limited to analysis of liquid/solution phases and are not suitable for vapour phase detection. Furthermore, these techniques may be slow to give a result, or may involve complex, expensive and/or non-portable equipment. Some techniques may also require careful sample preparation prior to analysis.

An alternative approach relies on molecular fluorescence. Vapor phase detection of N-methamphetamine has been reported by M. He et al., Fabrication of a new fluorescent film and its superior sensing performance to N-methamphetamine in vapor phase, Sensor and Actuators B 227 (2016) 255-262. This describes a fibrous network of a fluorescent compound. The compound is described as being a rational combination of a perylene bisimide derivative and cholesterol. The compound is said to exhibit fluorescence quenching in the presence of N-methyl-phenethylamine, a structural simulant of N-methamphetamine. It is indicated that the fibrous network is important as it enables fluorescent centres of the sensing compound to be accessible to the analyte.

Another approach based on molecular fluorescence is discussed by D. Wen et al., Fine structural tuning of fluorescent copolymer sensors for methamphetamine vapor detection, Sensors and Actuators B 168 (2012) 283-288. This publication describes the fluorescence quenching response of particular conjugated copolymers in the presence of methamphetamine.

The copolymers comprise repeat units consisting of a fluorenyl moiety and specified aryl moieties. It is noted that fluorene is chosen for the polymer backbone construction to achieve photo-induced electron transfer (PET) with respect to methamphetamine. The aryl moieties are noted as being electron deficient units (i.e., electron accepting) and are said to fine tune the highest occupied molecular orbital of the polymer and thus adjust the PET between the copolymer and methamphetamine. It is also suggested that the photophysical and electrochemical properties of the polymer are tunable by the alternating copolymerisation. Three copolymers are described specifically with molecular weights of 14900, 26000, and 5900. The difference in fluorescent response of each of the polymers to methamphetamine is attributed to the electron accepting units present. The data given indicate a detection limit only as low as 180 ppb may be achieved.

Shi et al. (High performance aniline vapor detection based on multi-branched fluorescent triphenylamine-benzothiadiazole derivatives: branch effect and aggregation control of the sensing performance, J. Mater. Chem. 2012, 22, 11629) describe a series of sensory materials consisting of a donor-acceptor conjugated structure for detection of aniline vapor. Specifically, three compounds are described each including a triphenylamine (TPA) donor moiety as a "core" moiety with 1, 2 or 3 benzothiadiazole-pyridine (BP) branches as acceptor moiety/moieties. The compounds are tested in solution and in film form. It is suggested that electrons can delocalize over all conjugated branches in such donor-acceptor structures. It is noted that with increasing BP moieties, severe aggregation in the film occurred which retards vapor penetration and decreases active contact area. A nano-structured substrate (vertically oriented ZnO nanorods, 80 nm in diameter) was used to decrease aggregation and increase sensing performance. It is noted that when cast on the nano-structured substrate TPA3BP showed a 100 fold and 1000 fold decreased limit of detection to aniline vapor when compared with TPA2BP and TPABP. From this it is concluded that morphology control is an important aspect for the compounds described.

It would be desirable to provide further alternatives for detection of narcotics. It would be particularly desirable to provide detection capability that has high selectivity in the presence of typical interferents and that has suitably high sensitivity. It would be very desirable to provide detection capability that has at least the same detection sensitivity as existing techniques, and preferably higher. Providing detection sensitivity at concentrations of lower than 50 ppb would be particularly advantageous.

SUMMARY OF THE INVENTION

In one aspect, the present invention provides an optical sensing element for detection of a narcotic, the optical sensing element comprising a fluorescent sensing compound provided on a substrate, wherein emission of the fluorescent sensing compound is quenched in the presence of the narcotic, and wherein the fluorescent sensing compound is non-polymeric and comprises an electron donor moiety, an electron acceptor moiety and a moiety that influences solubility of the compound in a solvent. In an embodiment, in addition to influencing solubility, the moiety may also influence how the sensing compound interacts with the analyte (narcotic). In some embodiments, the optical sensing element is for vapour phase detection.

The present invention also provides a method for detection of a narcotic in a sample, which method comprises: (a) irradiating an optical sensing element in accordance with the present invention thereby causing fluorescent emission by the fluorescent sensing compound; (b) contacting the sample with the optical sensing element; (c) measuring the luminescence of the fluorescent optical sensing element after contacting with the sample; and (d) determining whether the narcotic is present in the sample based on the measurement obtained in step (c). The optical sensing element is irradiated continuously or with pulses at least during steps (b) and (c). The sample may be treated to convert any narcotic present to a free base form. In some embodiments, the method is for vapour phase detection.

The present invention also provides a sensing device in which the optical sensing element would be used. Accordingly, in this embodiment the present invention provides a sensing device for detection of a narcotic in a sample, the sensing device comprising: an optical sensing element in accordance with the present invention;

an irradiation source for irradiating the optical sensing element with stimulating radiation;

a detector for measuring luminescence of the optical sensing element;

means for delivering the sample for contacting with the optical sensing element; and means for relating to an operator the luminescence measured by the detector. The sensing device may additionally comprise means for converting any narcotic present in the sample to a free base form. In some embodiments, the sensing device is for vapour phase detection.

The invention may have application in law enforcement applications where detection of narcotics is important.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

BRIEF DISCUSSION OF DRAWINGS

Embodiments of the present invention are illustrated with reference to the accompanying non-limiting drawings in which:

FIG. 1 is a schematic illustrating a device useful in implementing detection of narcotics according to an embodiment of the present invention.

Figure 2A:
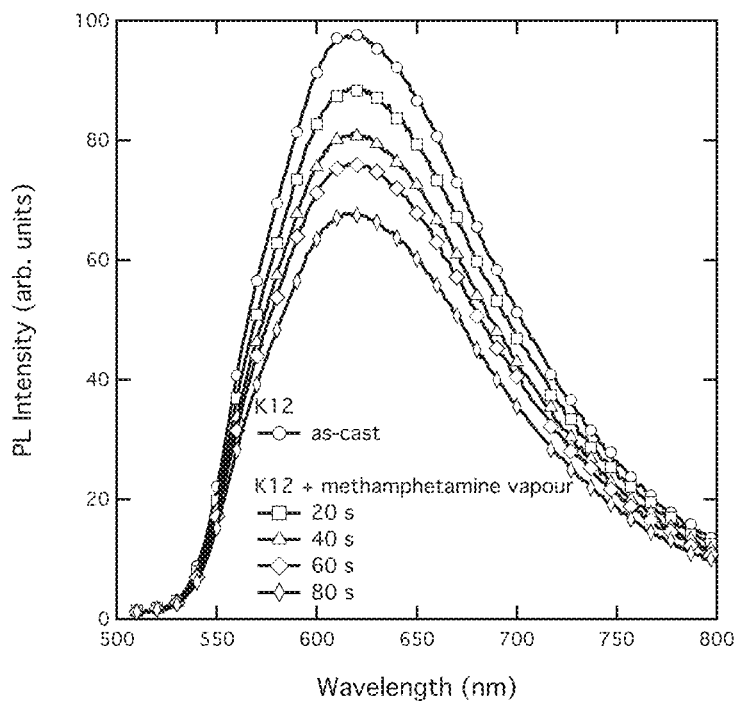
Figure 2B:
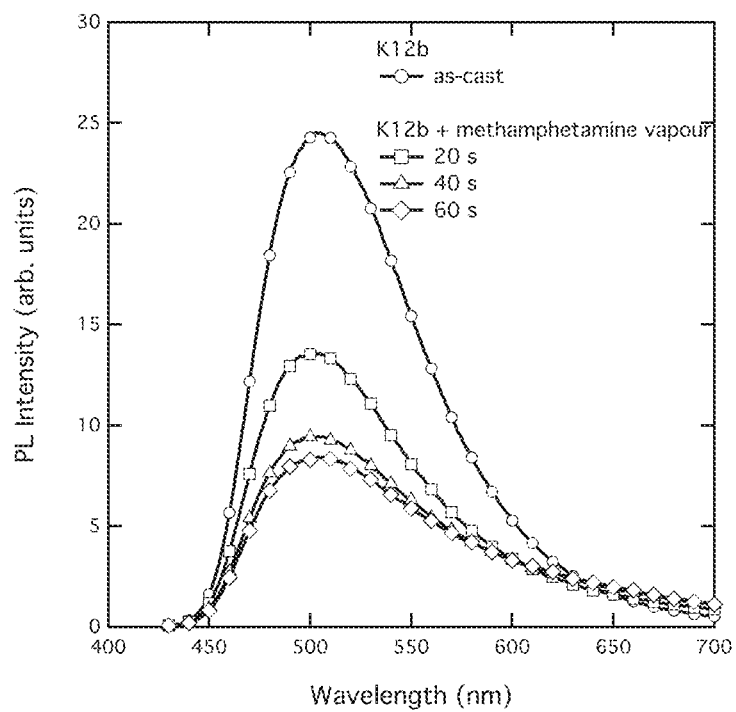
Figure 2C:
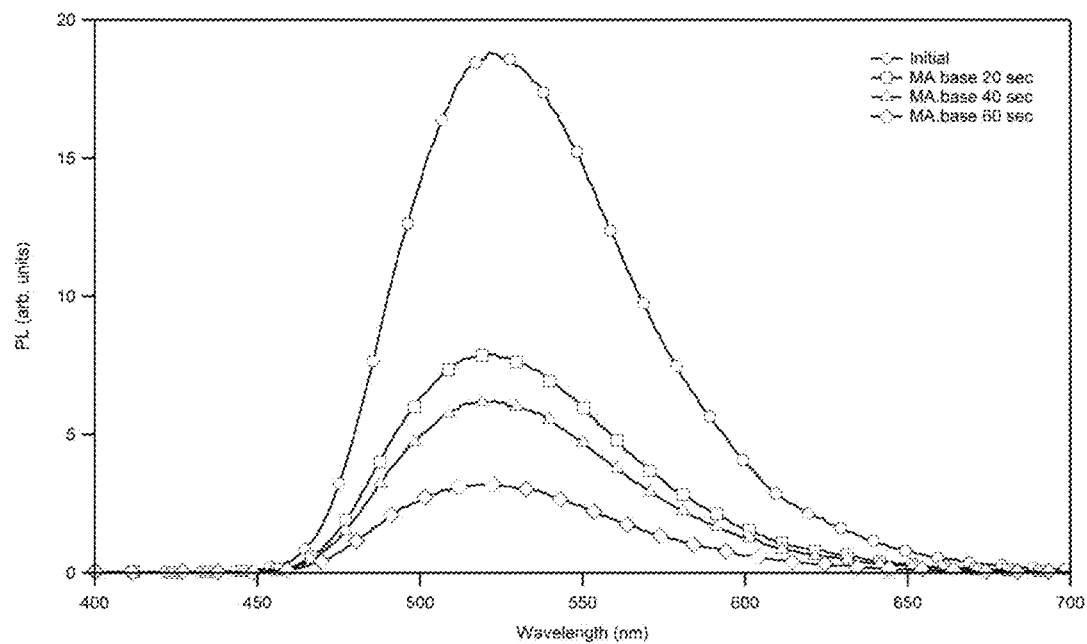
Figure 2D:
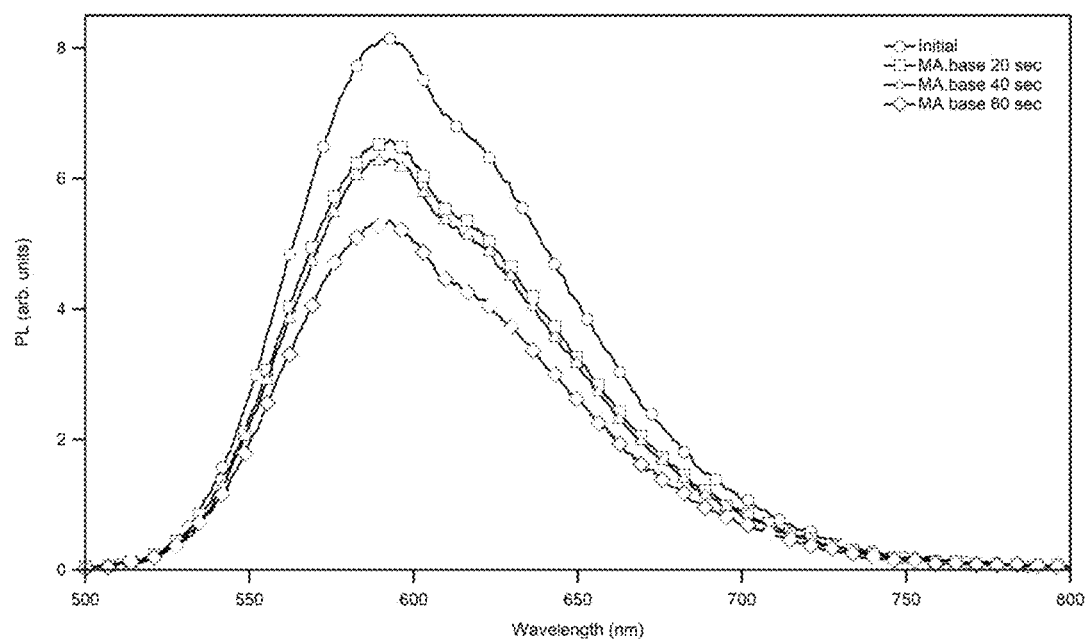
Figure 2E:
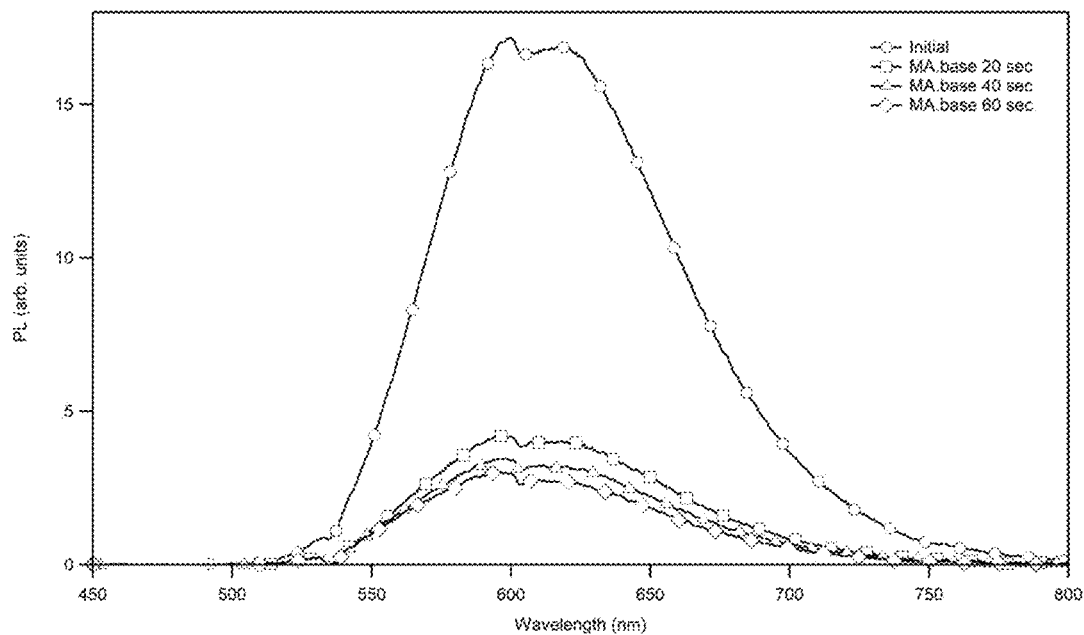
Figure 2F:
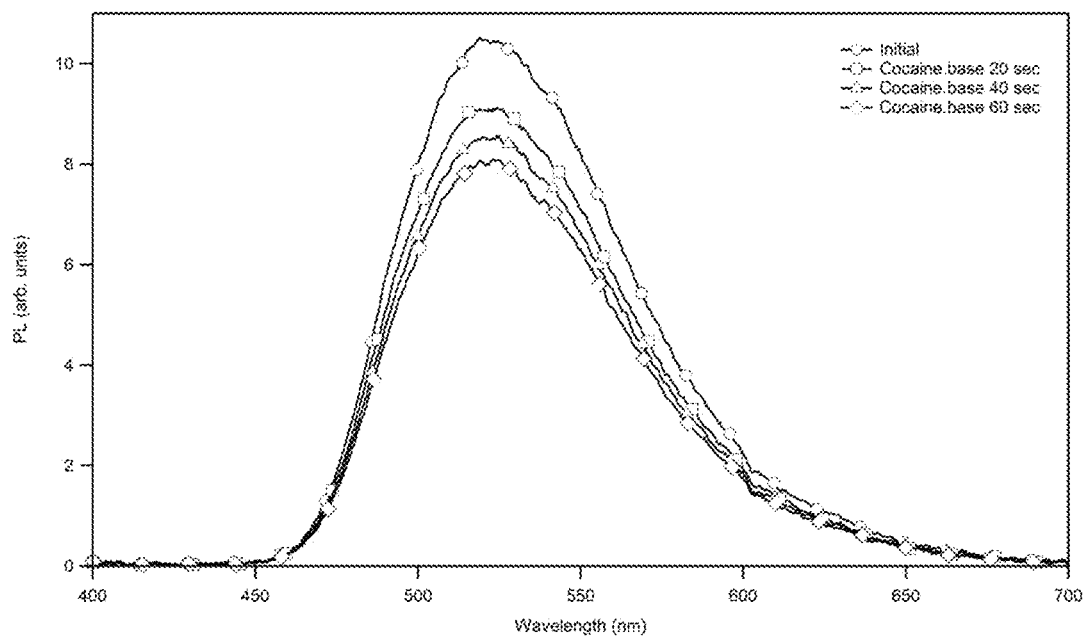
Figure 2G:
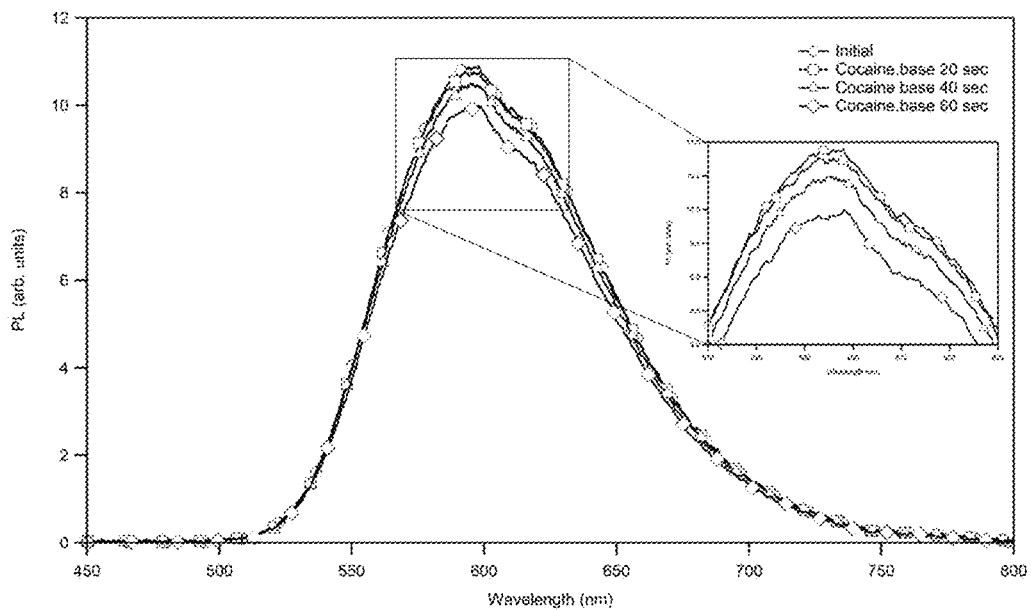
Figure 2H:
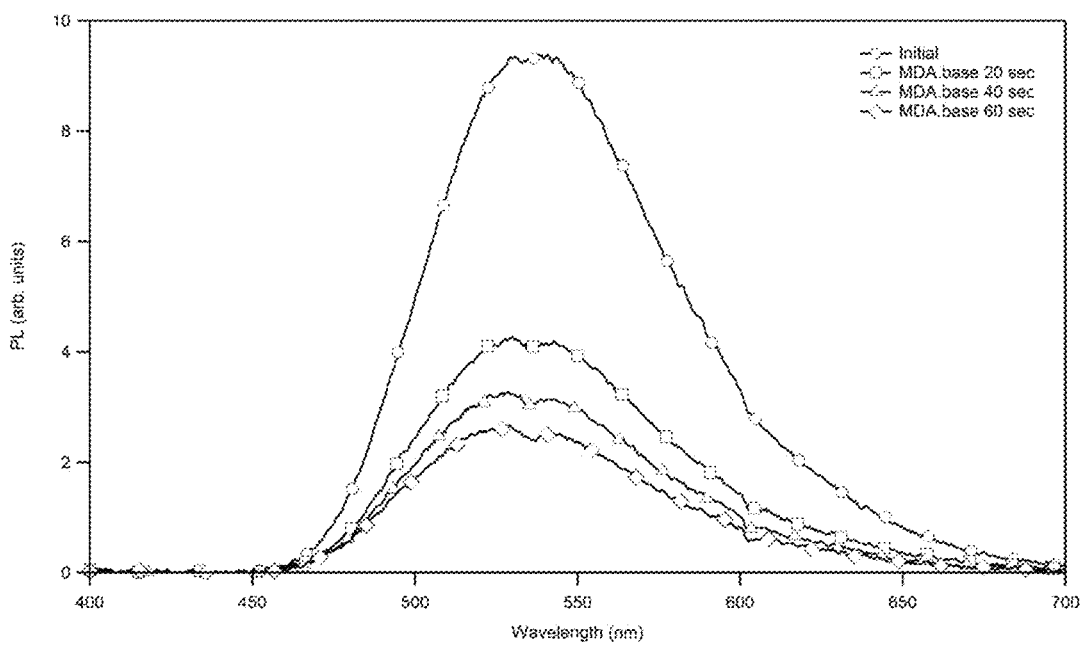
Figure 2I:
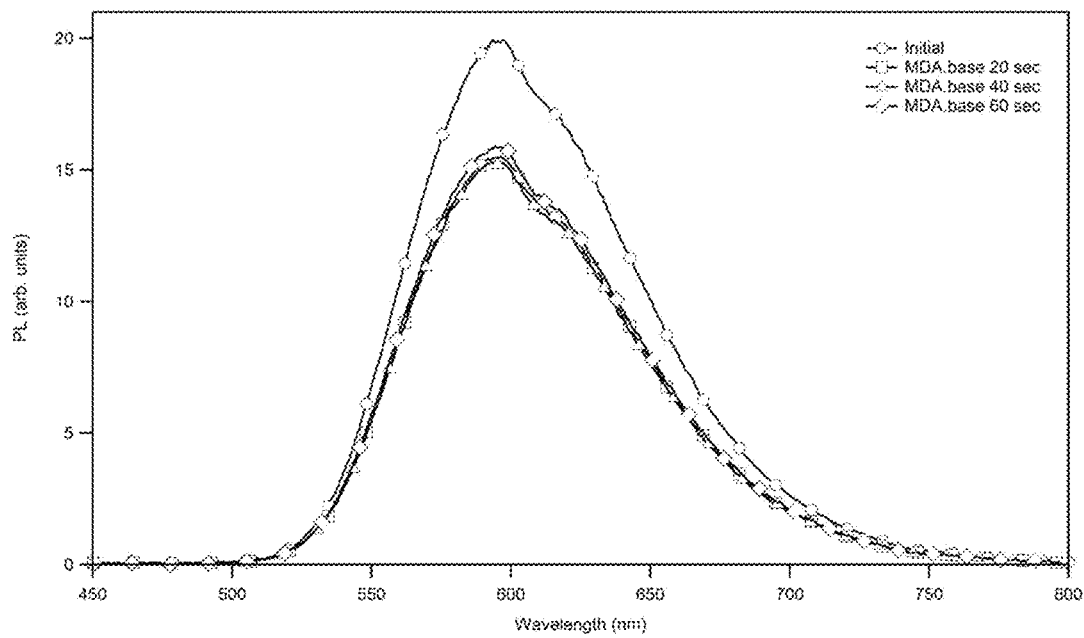
Figure 2J:
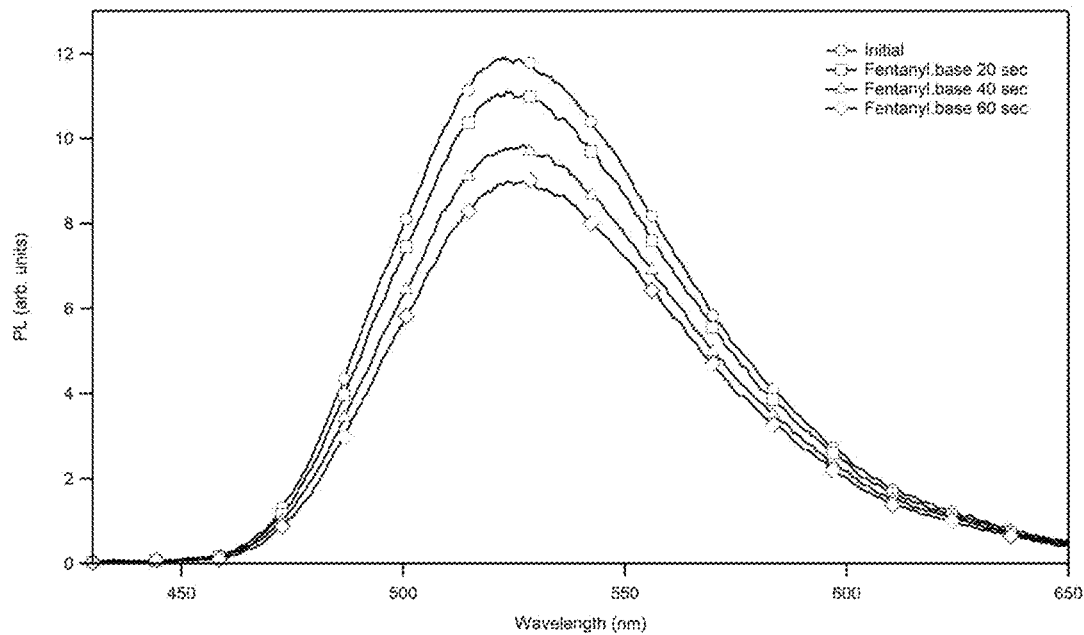
Figure 2K:
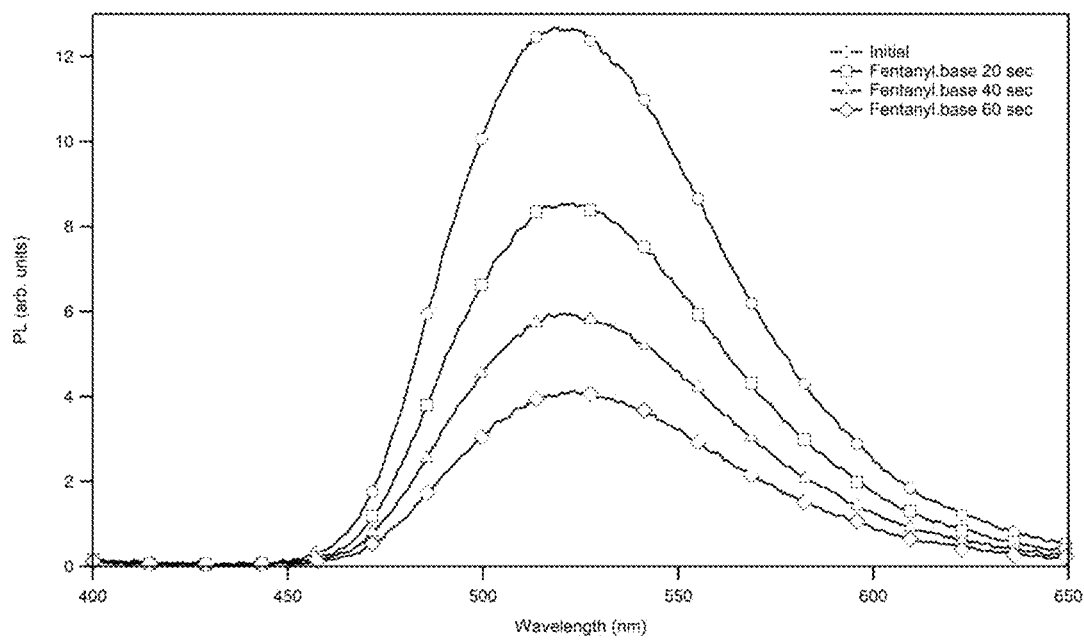

FIGS. 2a to 2k are a series of graphs showing the change in fluorescence of a film of a sensing compound in the presence of a narcotic vapour demonstrating quenching in the presence of the narcotic analyte. FIGS. 2a to 2e demonstrate quenching of the compounds K12 (FIG. 2a); K12b (FIG. 2b); AL03-96 (FIG. 2c); AL04-09 (FIG. 2d) and JED (FIG. 2e) in the presence of methamphetamine free base held at room temperature (approximately 22° C.). FIGS. 2f and 2g demonstrate quenching of the compounds AL03-96 (FIG. 2f) and AL04-09 (FIG. 2g) in the presence of cocaine free base held at 90° C. FIGS. 2h and 2i demonstrate quenching of the compounds AL03-35 (FIG. 2h) and AL04-09 (FIG. 2i) in the presence of 3,4-dimethylenedioxyamphetamine (MDA) free base held at 30° C. FIGS. 2j and 2k demonstrate quenching of the compound AL03-116 (FIG. 2j) and AL03-96 (FIG. 2k) in the presence of fentanyl free base held at approximately 160° C.

Figure 3A:
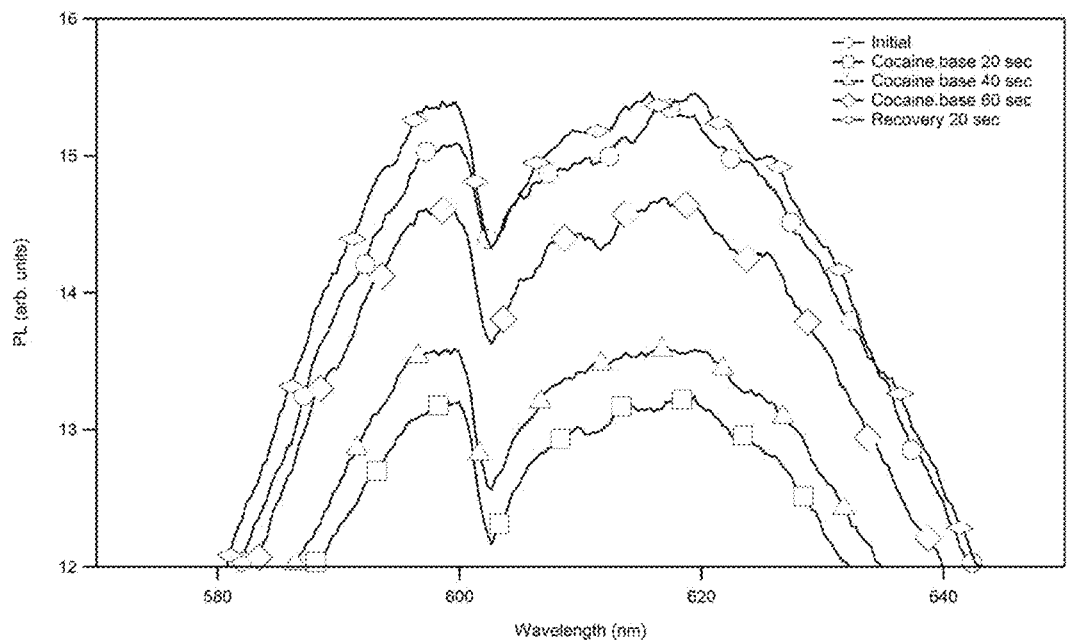
Figure 3B:
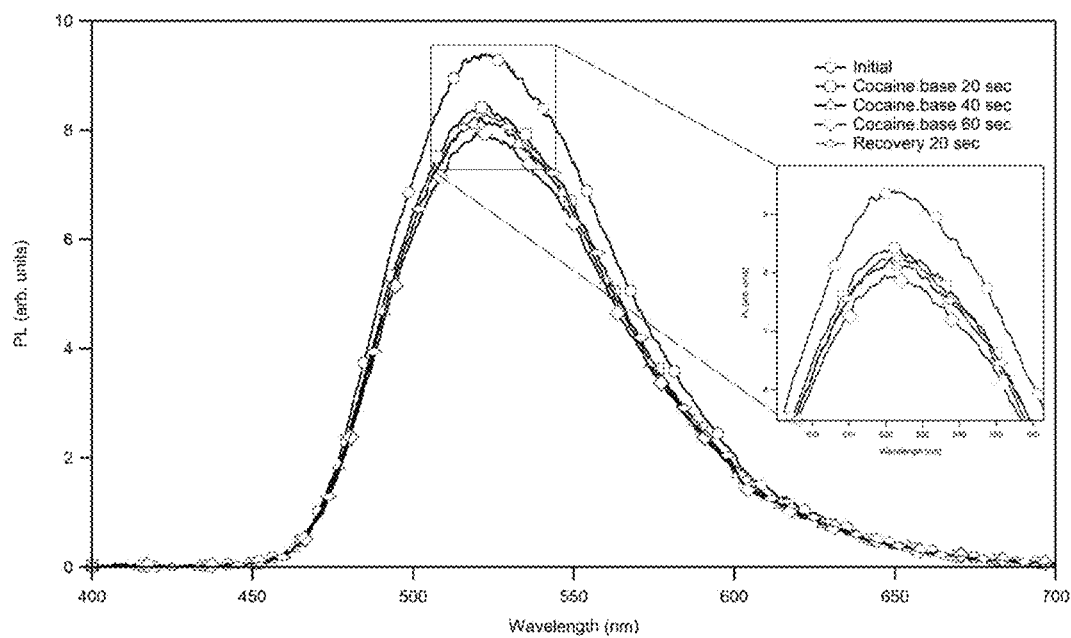
Figure 3C:
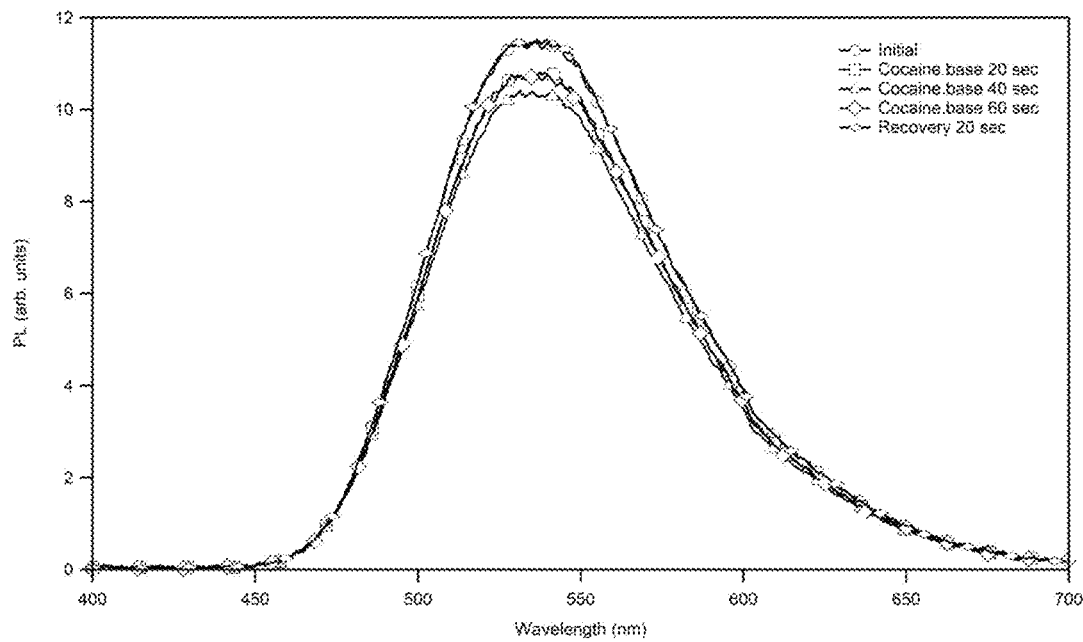
Figure 3D:
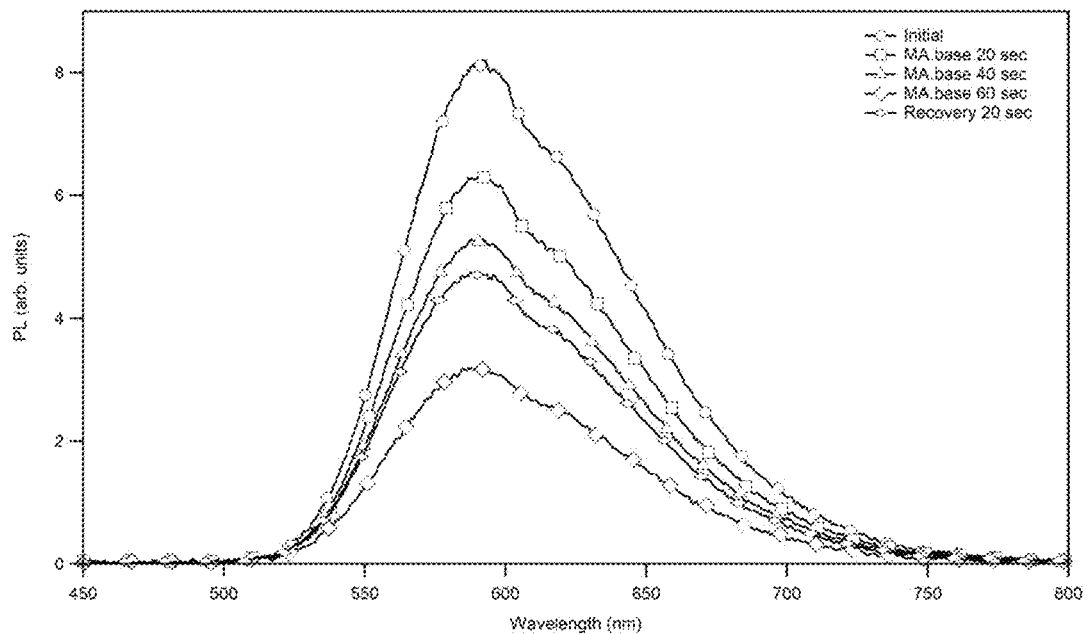
Figure 3E:
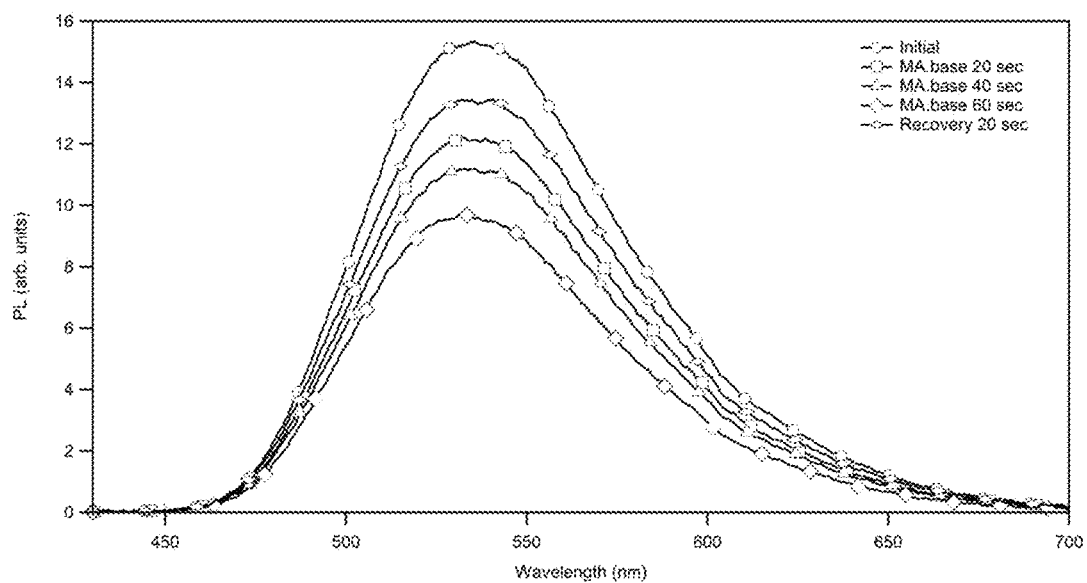
Figure 3F:
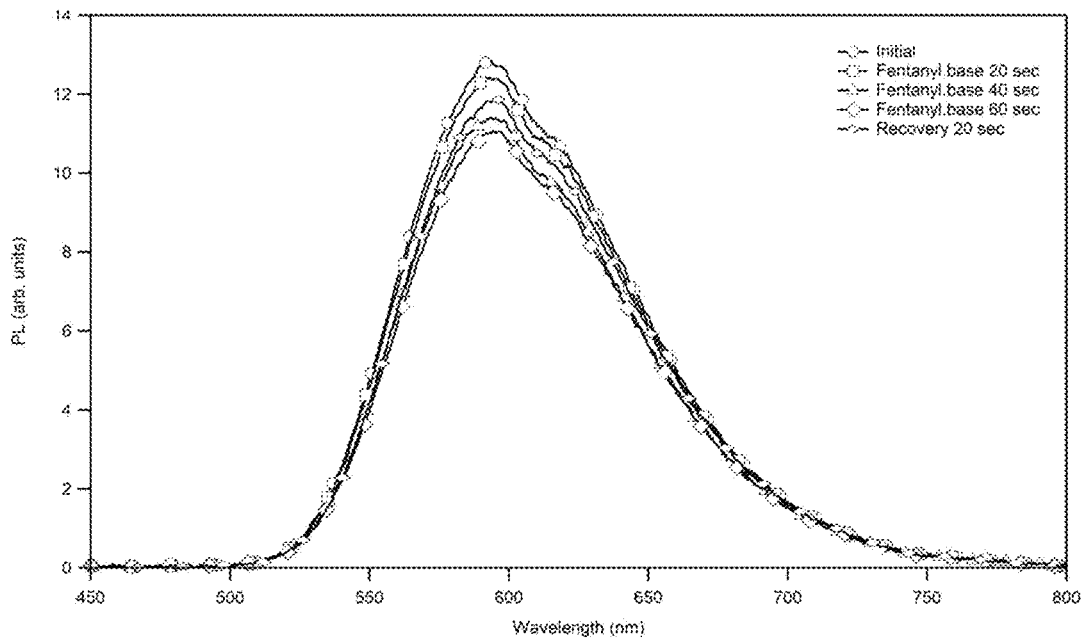
Figure 3G:
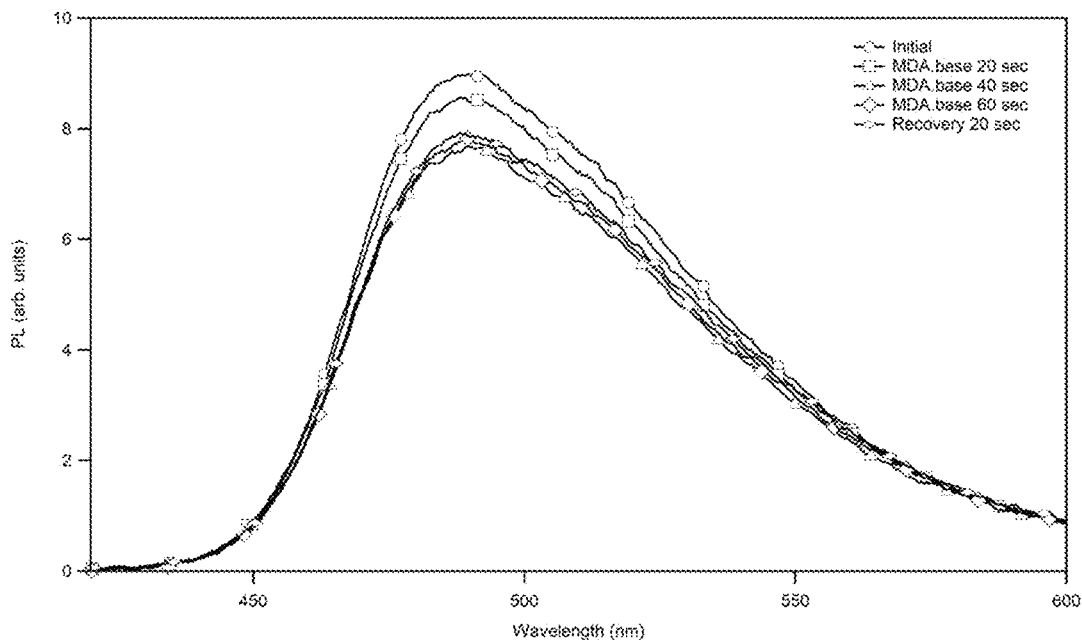
Figure 4A:
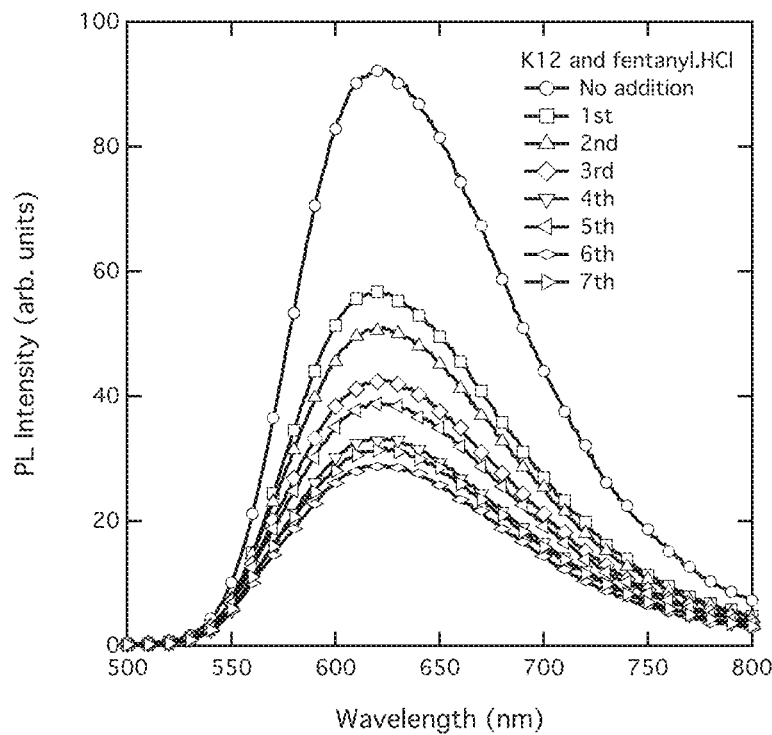
Figure 4B:
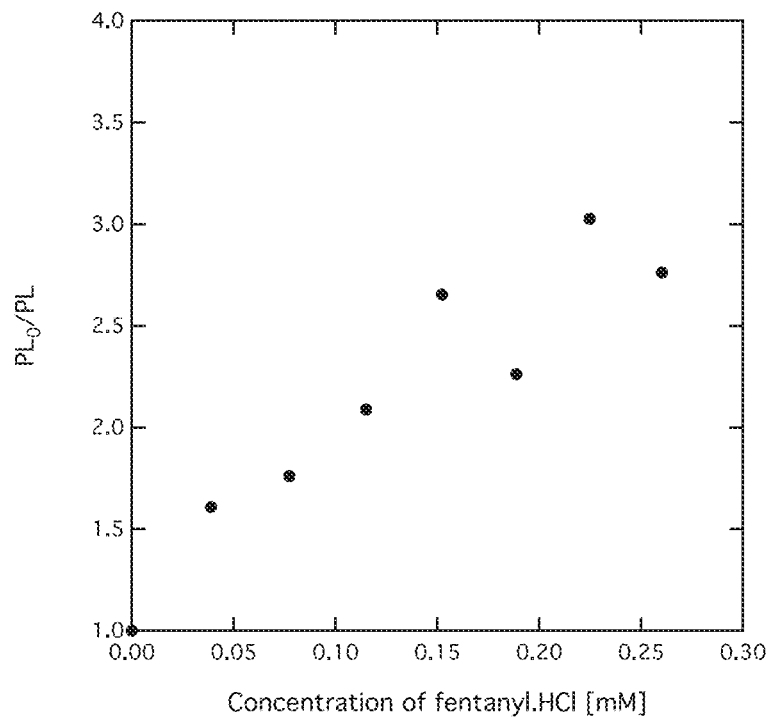

FIGS. 3a to 3g show a series of graphs illustrating the change in fluorescence of a sensing film of a sensing compound in the presence of a narcotic vapour demonstrating quenching in the presence of the narcotic analyte. Sensing films were then removed from the analyte source to demonstrate the reversibility of the quenching process. The figures show the initial film luminescence, the decrease in luminescence after 60 seconds exposure to the analyte and the recovery of the luminescence that has occurred after 20 seconds. FIGS. 3a-3c demonstrate quenching of sensing compounds JED (FIG. 3a); AL03-96 (FIG. 3b); and AL03-35 (FIG. 3c) in the presence of cocaine free base analyte held at about 90° C., and subsequent recovery of luminescence following removal of the analyte source. FIG. 3d and FIG. 3e respectively illustrate the behavior of sensing compounds AL04-09 and AL03-35 in the presence of methamphetamine free base analyte held at room temperature (about 22° C.), and subsequent recovery of luminescence following removal of the analyte source. FIG. 3f illustrates the quenching of the sensing compound AL04-09 in the presence of fentanyl free base held at about 160° C., and subsequent recovery of luminescence following removal of the analyte source; and FIG. 3g illustrates the quenching of the sensing compound K12b in the presence of MDA free base held at about 30° C., and subsequent recovery of luminescence following removal of the analyte source. FIG. 4a is a graph showing the change in fluorescence of compound K12 in the presence of an increasing concentration of fentanyl hydrochloride in water demonstrating fluorescence quenching in the presence of the analyte. FIG. 4b shows the corresponding $PL_0/PL$ values plotted against the concentration of fentanyl hydrochloride.

Figure 5A:
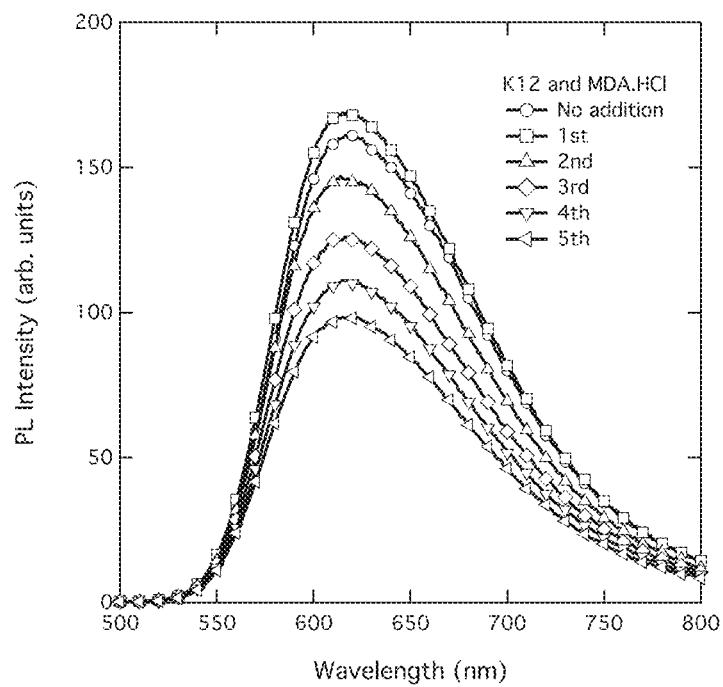
Figure 5B:
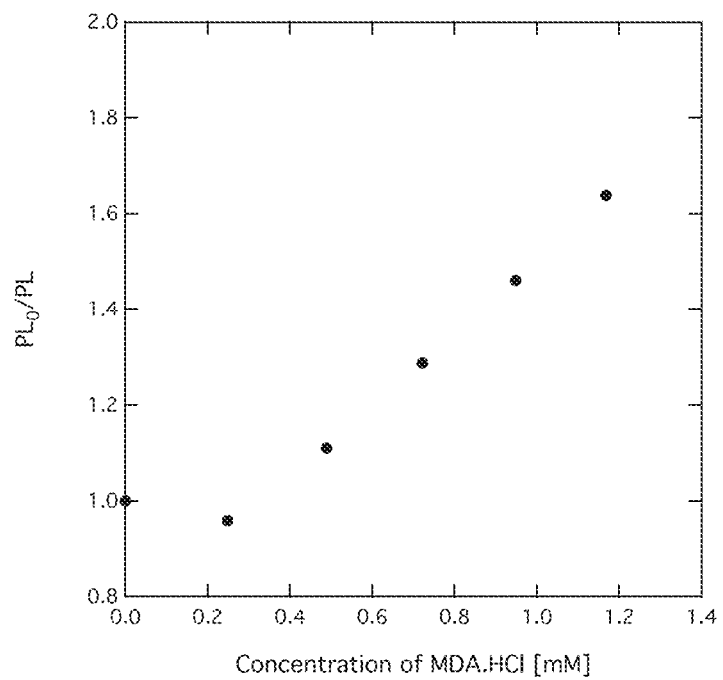

FIG. 5a is a graph showing the change in fluorescence of compound K12 in the presence of increasing concentrations of MDA.HCl (3,4-methylenedioxyamphetamine hydrochloride) in water. Quenching of the fluorescence is demonstrated in the presence of the analyte. FIG. 5b shows the corresponding $PL_0/PL$ values plotted against the concentration of MDA.HCl.

Figure 6A:
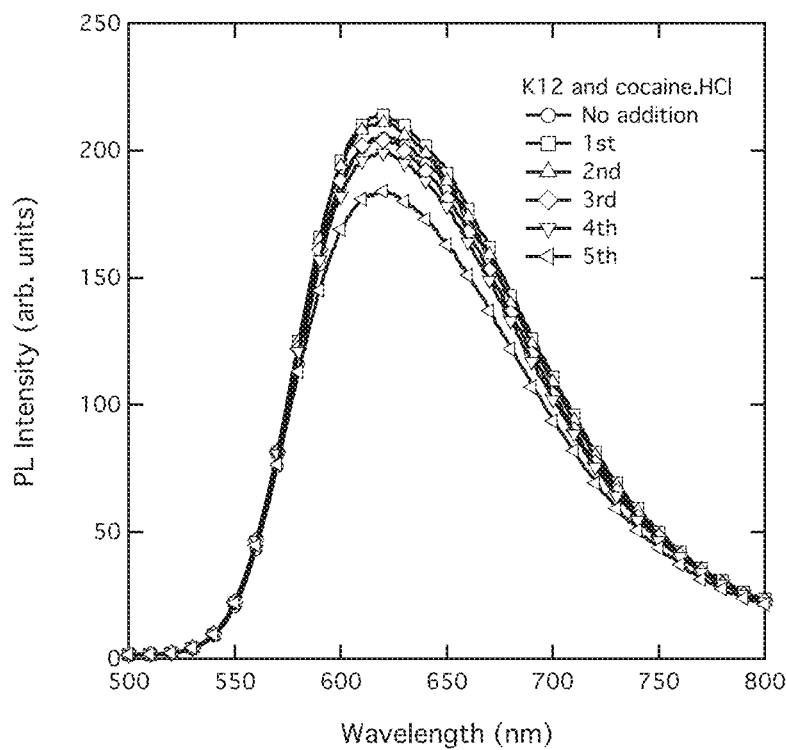
Figure 6B:
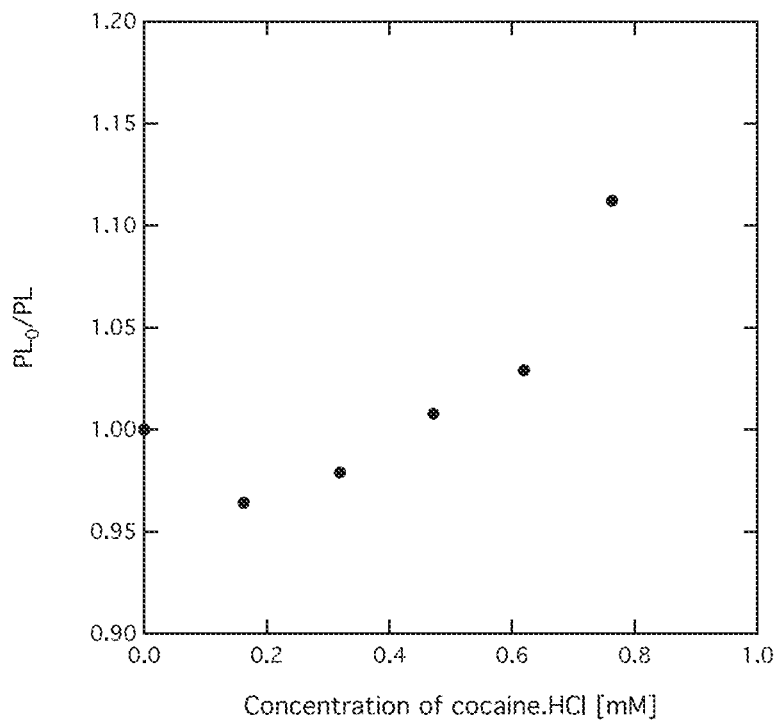

FIG. 6a is a graph showing the change in fluorescence of compound K12 in the presence of increasing concentrations of cocaine hydrochloride in water. Quenching of the fluorescence is demonstrated in the presence of the analyte. FIG. 6b shows the corresponding $PL_0/PL$ values plotted against the concentration of cocaine hydrochloride.

DETAILED DISCUSSION OF THE INVENTION

In accordance with the present invention the presence of a narcotic can be detected based on the luminescent response of an optical sensing element when exposed to the narcotic. More specifically, the fluorescent sensing compound of the optical sensing element can be photoexcited thereby causing a characteristic fluorescent emission. However, when the photoexcited compound is exposed to the narcotic, a quenching of the fluorescent emission occurs. This quenching can be detected and relied upon as an indicator for the presence of the narcotic. It has been discovered that this form of narcotic detection has application for detection of narcotics in the vapour phase. It is also applicable to solution phase detection, for example detection of a narcotic in an aqueous solution. This adaptability thus provides access to a variety of methods for detecting narcotics which can be adjusted to suit various situations.

In this specification the term "narcotic" is used in the conventional sense to denote an addictive drug that is prohibited by law. The present invention may be used to detect a variety of narcotics based on the interaction of the narcotic with the photoexcited fluorescent sensing compound. Examples of narcotics that may be detected in accordance with the present invention include one or more of:

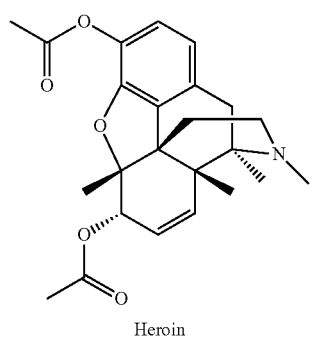

Heroin

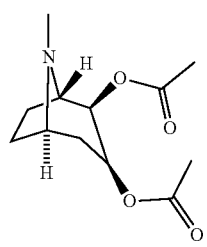

Cocaine

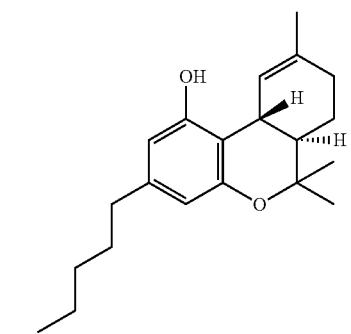

THC (Dronabinol - main ingredient of cannabis)

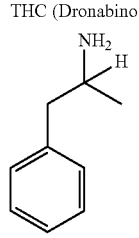

Amphetamine

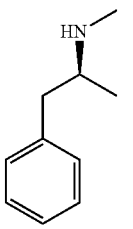

Methamphetamine

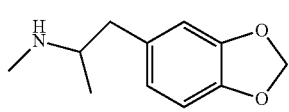

MDMA (Ectasy)

Ketamine

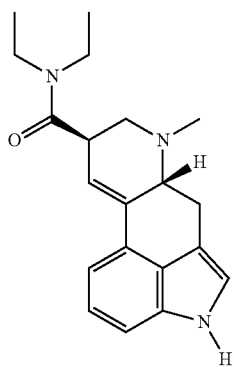

LSD

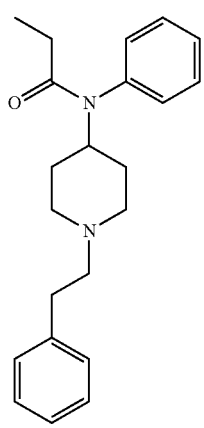

Fentanyl

-continued

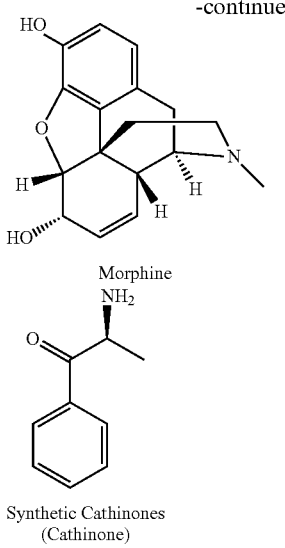

Morphine

Synthetic Cathinones
(Cathinone)

Such narcotics may exist as their free base or may be in the form of an acid addition salt, such as a hydrochloride salt. In accordance with the methods described herein, the narcotic analyte may be detected regardless of whether the narcotic is present as its free base or as an acid addition salt, such as a hydrochloride salt. In general, it will be appreciated that detection of a narcotic in the form of a salt may require heating to a higher temperature than that required for the corresponding free base to effect vaporisation. In some examples it may be necessary to heat a narcotic salt to a temperature of greater than 120° C. or greater than 140° C. to enable vaporisation. When analyzing a sample in accordance with the invention, it will be appreciated that it may be desirable to convert any narcotic present as an acid addition salt to its free base prior to carrying out analysis of the sample. Methods of converting a hydrochloride salt to the corresponding free base are well known in the art and include techniques such as heating, or reaction with a base.

The fluorescent sensing compound used in the present invention is non-polymeric in character. As essential structural features the fluorescent sensing compound comprises at least one electron donor moiety and electron acceptor moiety. These moieties are primarily responsible for the fluorescence quenching effect of the sensing compound, and the mechanism responsible for this is explained in more detail below. The fluorescent sensing compound also includes another functional moiety that is selected based on its effect on solubility of the sensing compound in a solvent. As will be explained, this is relevant to how the sensing compound is provided on a substrate. The choice of functional moiety/moieties will influence the type of solvent that may be employed to dissolve the sensing compound prior to providing a coating on the substrate. It is also possible that the functional moiety/moieties can provide an element of selectivity to the narcotic detected. For example, a functional moiety that is lipophilic in nature may give increased selectivity to narcotics that are relatively more lipophilic than other narcotics, such as THC. On the other hand, a functional moiety that is more polar in nature may give increased selectivity to narcotics that are more polar in character. The sensing compound may include one or more such functional moieties that are the same or different. It will be appreciated that the degree of interaction and/or selectivity between a given functional moiety/moieties and a given narcotic may vary depending on whether the detection is performed in a solution or vapour phase. It will also be understood that a sensing compound for use in a solution-based detection method preferably has negligible solubility in the solvent employed.

The compound may include more than one electron donor moiety and more than one electron acceptor moiety. However, in that case the compound does not include repeat units comprising these moieties to the extent that it may be regarded as a polymer. In an embodiment the compound may include repeat units comprising electron donor and electron acceptor moieties with the degree of repetition of those units being up to 5. Each repeat unit may comprise one or more electron donor moieties and one or more electron acceptor moieties. Electron donor moieties are defined as having a lower electron affinity and ionisation potential. Electron acceptors moieties are defined as having high electron affinity and ionisation potential.

The fluorescent sensing compound may include one or more modifier moieties that enable fine tuning of optoelectronic properties of the sensing compound in the context of the present invention. The role of this modifier moiety is to influence how the sensing compound interacts with a narcotic resulting in a fluorescence quenching effect. The one or more modifier moieties influence the electron affinity of the photoexcited sensing compound with respect to a particular narcotic. This may enable the selectivity of the sensing compound to be adjusted.

The fluorescent sensing compound may include a branching moiety from which branches comprising the electron donor and electron acceptor moieties extend. In this case it is possible that the branches may include a functional moiety of the type mentioned.

Noting these possibilities, the fluorescent sensing compound may be represented by general formula (I):

$$A_a B_b C_c D_d E_e \qquad (I)$$

in which:
A is an electron donor moiety;
B is an electron acceptor moiety;
C is a moiety that influences solubility of the compound in a solvent;
D is a modifier moiety that enables fine tuning of the optoelectronic properties of the sensing compound;
E is a branching moiety;
a is an integer of 1 or more;
b is an integer of 1 or more;
c is an integer of 1 or more;
d is an integer of 0 to less than or equal to b; and
e is 0 or 1.

The fluorescent sensing compound may be a dendrimer having a "core" comprising one or more of the electron donor and/or electron acceptor moieties with dendron moieties attached to the core. The dendron moieties may comprise functional moieties of the types mentioned. The dendrons can be first, second or higher generations, with surface groups chosen to provide the necessary solubility and interactions with the analyte.

Formula (I) is an empirical formula and should not be interpreted as implying any particular sequence or arrangement of moieties.

The compound may comprise more than one moiety A and more than one B moiety. In this case the formula given should not be interpreted as meaning that the compound necessarily includes repeat a unit-A-B-. This may be the case but other arrangements are possible. Other moieties, such as modifier moieties D, can be attached to either A or B, or both. When more than one moiety A is present, they may be the same or different. When more than one moiety B is present, they may be the same or different. When more than one D moiety is present, each D may be the same or different.

The fluorescent sensing compound may be a dimer, trimer or higher oligomer.

In an embodiment in formula (I), a is an integer of 1 to 5.

In an embodiment in formula (I), b is an integer of 1 to 5.

The moiety A is an electron donor moiety and non-limiting examples of this moiety include fluorenyl, bisfluorenyl, phenyl, thiophenyl, phenyl, and terphenyl.

The moiety B is an electron acceptor moiety and non-limiting examples of this moiety include benzothiadiazolyl, benzooxadiazolyl, oxazolyl, triazinyl, imidazolyl, pyridinyl and quinoxalinyl.

Examples of the moiety C include straight or branched chain alkyl or alkoxy groups containing up to 10 carbon atoms (preferably n-propyl groups), ethylene glycol chains including 2-methoxymethyl, 2-methoxyethyl, 2-(2-methoxyethoxy)ethyl, and 2-(2-(2-methoxyethoxy) ethoxy) ethyl. The moiety C may include one or more aryl rings (preferably phenyl) and/or hetero atoms, and/or heteroaryl, and/or alkenyl, and/or alkynyl. By way of example the group C may be an alkoxy group, such as $C_{1-10}$ alkoxy attached to a phenyl ring.

Examples of modifier moieties (D) that may be used in this way include Rhodanine, vinyl cyano esters, and vinyl dicyano vinyl diesters. In the vinyl cyano esters the ester moiety may include a $C_{1-8}$ alkyl group. In the vinyl diesters the alkyl groups may be the same or different $C_{1-8}$ alkyl groups.

In an embodiment A is fluorenyl and B is benzothiadiazolyl.

In an embodiment A is fluorenyl, B is benzothiadiazolyl and D is 1,1-dicyanovinyl.

The sensing compound may include moieties A and B and where present D in a linear arrangement. In this case, e is 0 and no branching moiety is present.

In an alternative the sensing compound may be a branched structure. In this case in formula (I), e is 1 and the sensing compound includes a branching moiety E to which are attached arms (branches) containing the A, B, C and optionally D and possibly other functional moieties. The number of arms is typically 2, 3, 4, or 6 per molecule of the sensing compound.

In one embodiment the branching moiety is chosen such that each arm behaves as an individual chromophore within the sensing compound. That is, while the sensing compound may be fully conjugated the arrangement of arms is such that the wave functions are not fully delocalized. This can be achieved by having a linking moiety that does not contain conjugated units between the arms, and the use of regio-isomers that break the delocalization such as a meta arrangement of units around a benzene ring, or the use of steric interactions that twist the units out of plane. In an embodiment the branching moiety is a benzene ring substituted by the arms at the 1-, 3- and 5-positions. In another embodiment the branching moiety is a benzene ring itself hexa-substituted by phenylene moieties that form part of the arms. In another embodiment the branching moiety may be an adamantyl moiety tetra-substituted by phenylene moieties which also forms part of the arms. It will be appreciated that for branched sensing compounds branching moieties that cause delocalization of the pi-system are not preferred. Accordingly, in an embodiment compounds with a branching group that comprises a (central) nitrogen atom, such as a nitrogen atom or triphenylamine group, are not within the scope of the present invention because they delocalize the pi-systems of attached chromophores.

In a further embodiment the branched material may be a dendrimer comprised of a core, one or more dendrons (branching groups). The use of dendrons may enable the tuning of solubility and intermolecular interactions in the solid state. This may be relevant to controlling analyte diffusion and fluorescence quenching response. The dendrons can be first, second or higher generations, with surface groups chosen to provide the necessary solubility and interactions with the analyte. The dendrimer sensing compounds may have the core comprised of one or more of A and/or B moieties, and the dendrons themselves may contain one or more chromophores comprised of A and/or B and/or other functional moieties. In one embodiment the A moiety or moieties form the first branching point of the one or more dendrons. The dendrons can be comprised of aryl, heteroaryl, vinyl and/or acetylenyl units. For example, the dendron could be comprised of successive layers of 1,3,5-linked phenyl groups. Alternatively, these phenyl units could be linked by one or more (preferably one) vinyl or acetylenyl moieties. The surface groups could be comprised of C moieties.

It will be appreciated that the sensing compounds useful in the invention are generally relatively small molecules. Typically, the compounds will have a molecular weight of less than 3000 but if the compounds have a dendritic architecture the molecular weight could be higher.

Examples of fluorescent sensing compounds that may be useful in the present invention are given below.

The following are small molecule, linear compounds.

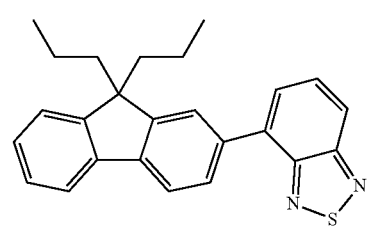

2.27

(FI-BT)

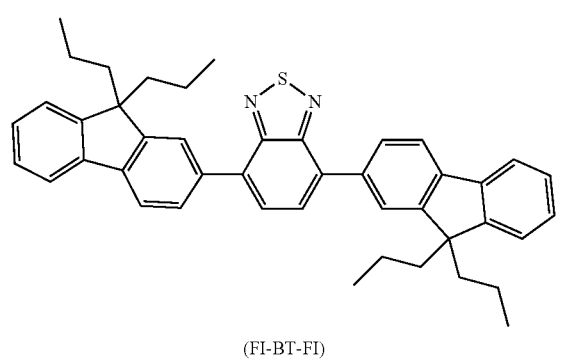

2.16

(FI-BT-FI)

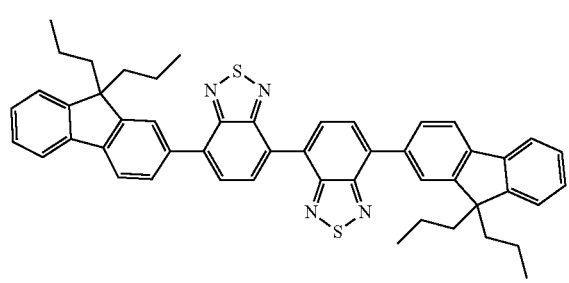
(Fl-BTBT-Fl)
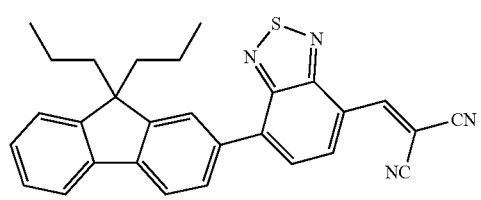
(K12)
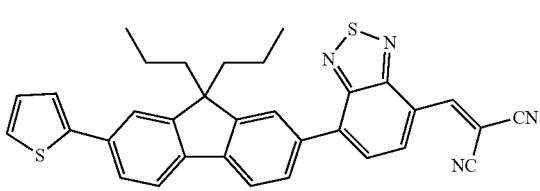
(K12-Th)
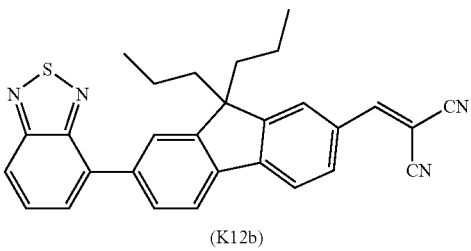
(K12b)
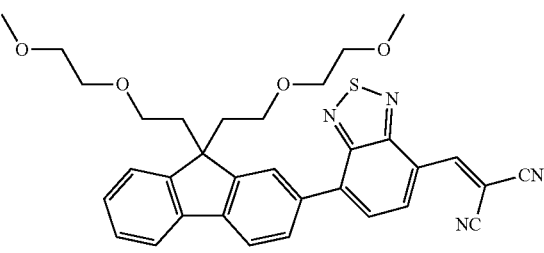
JED
The following are further examples of small molecule, linear compounds.
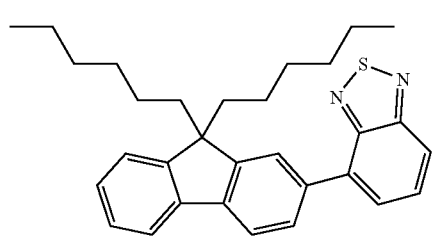
AL03-77
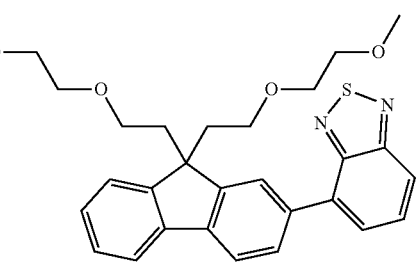
AL03-79
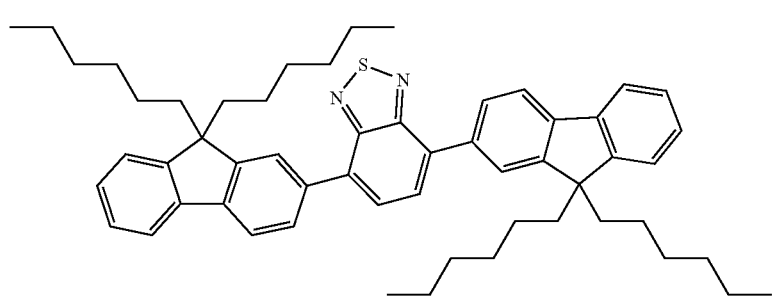
AL03-56

-continued
AL03-28
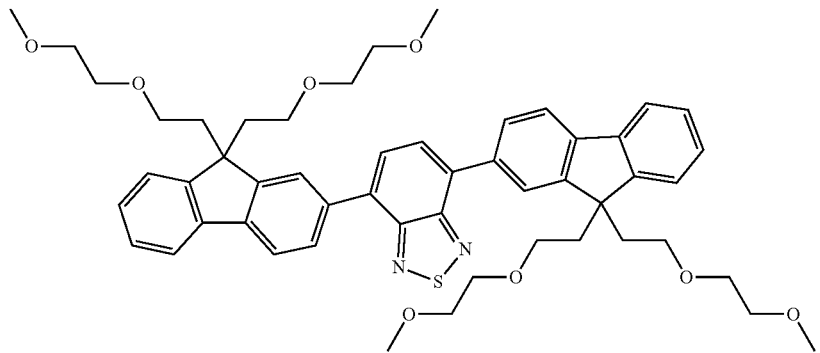
AL03-100
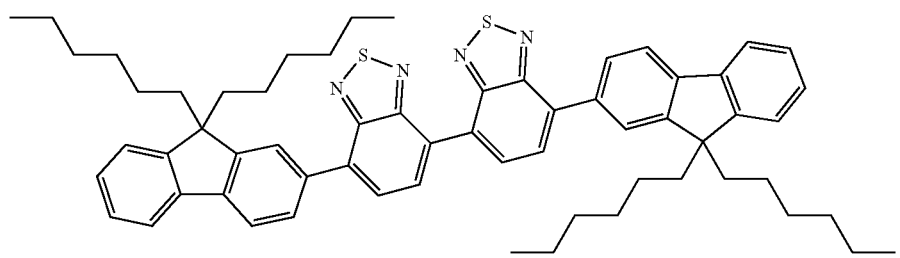
AL03-102
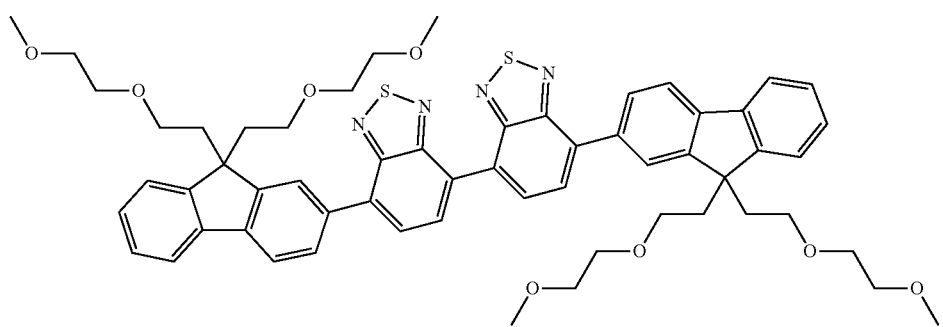
AL03-96
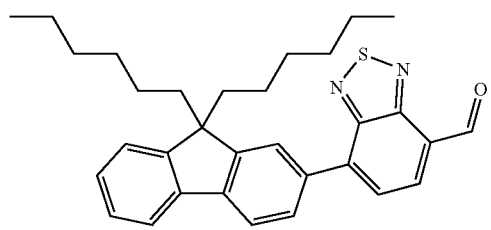
AL04-09
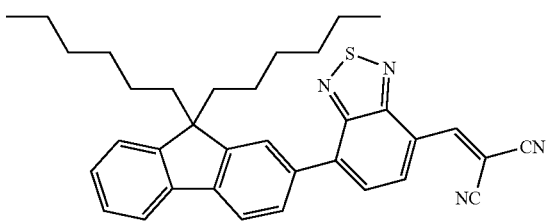
4.24
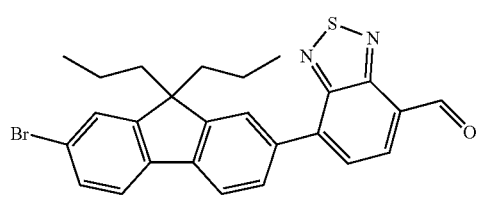
4.7
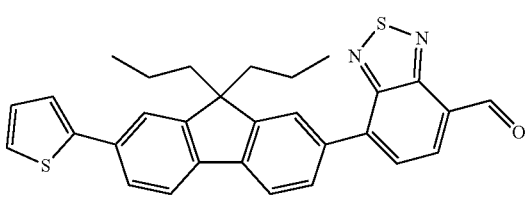

The following are branched molecules in which the electron donor and electron acceptor moieties are present in the branches.
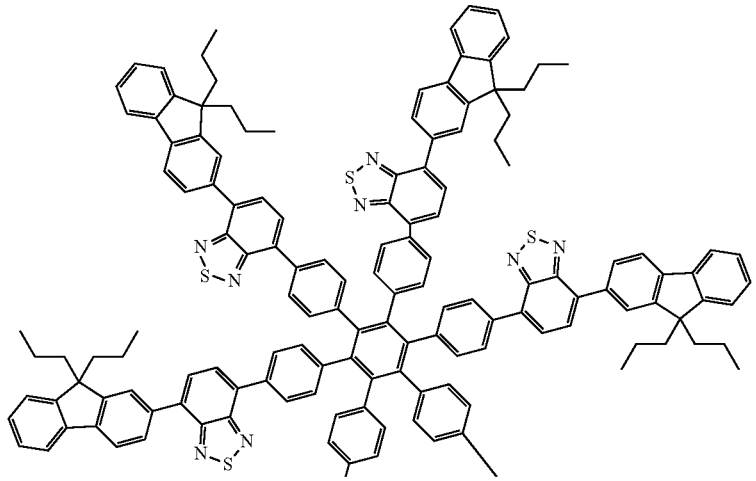
2.26
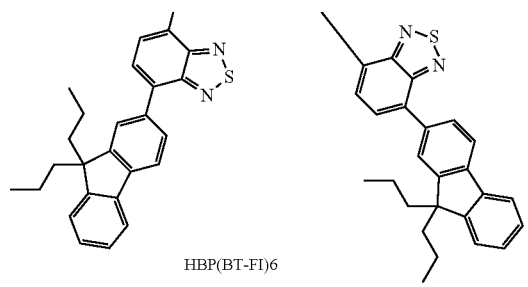
HBP(BT-Fl)6
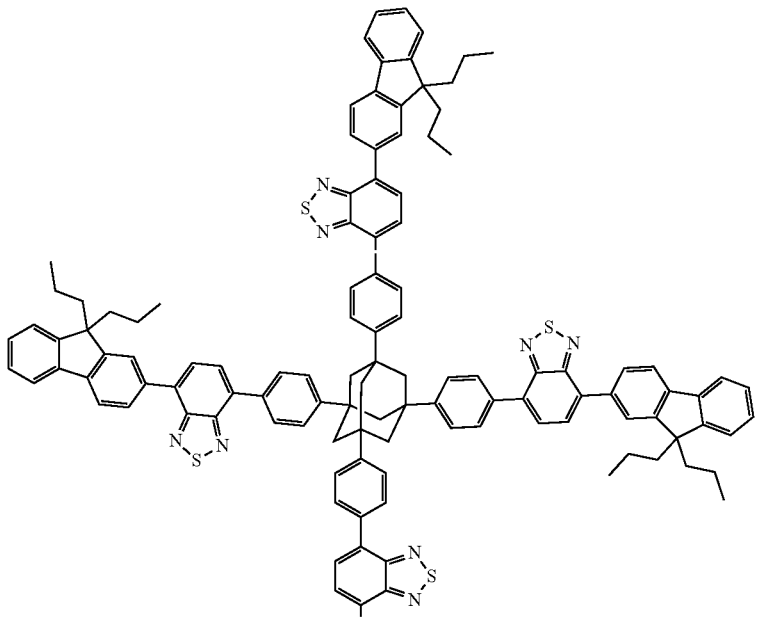
2.22

-continued
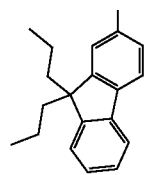
Ad(BT-Fl)4
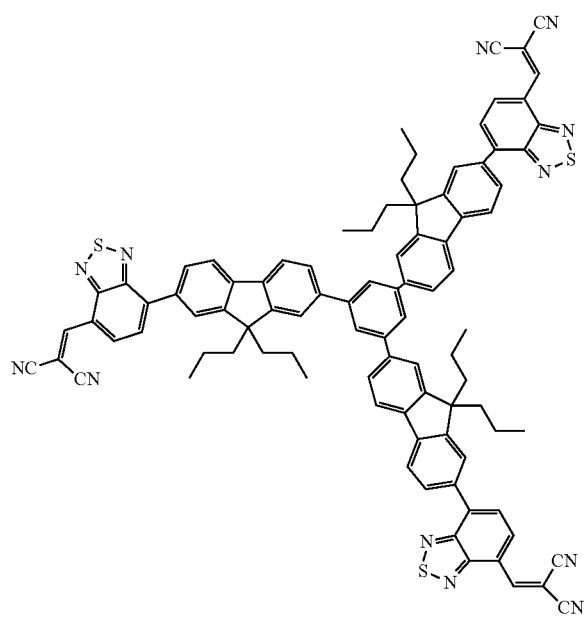
K12-3
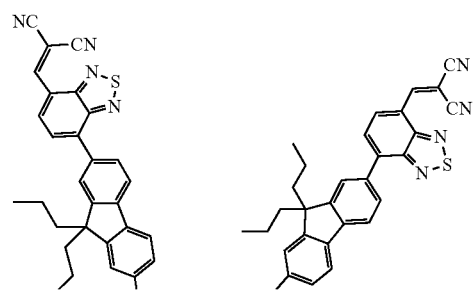
K12-6

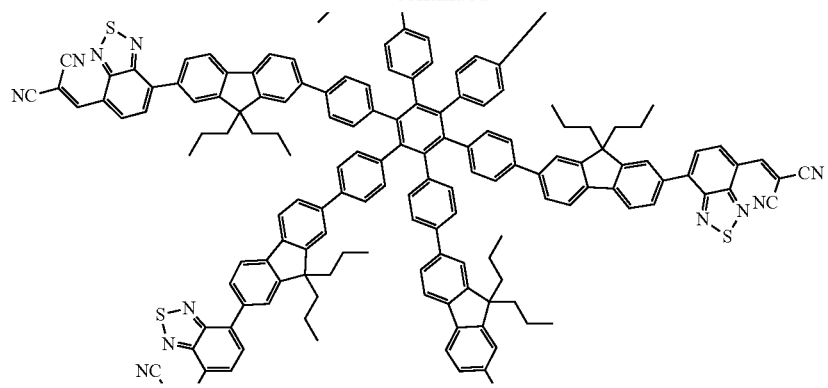
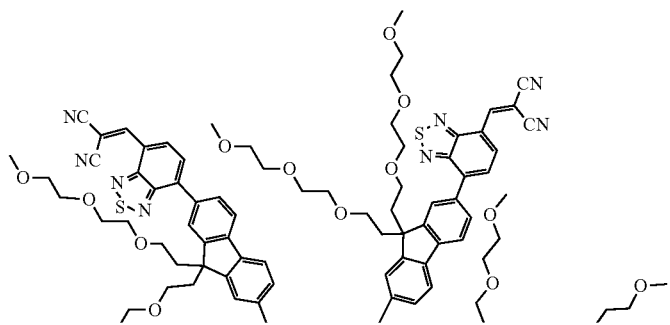
WJ07-24
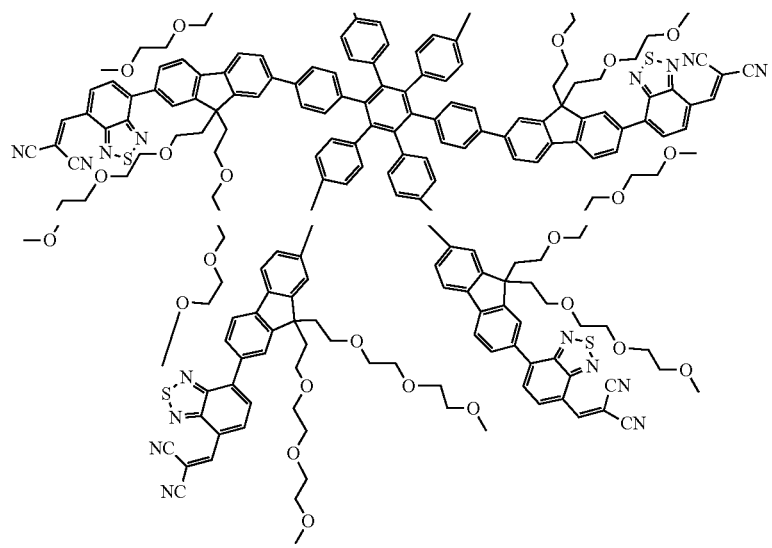

The following are dendrimers in which the electron acceptor moieties (B is benzothiadiazolyl and b is 1 or 2) are present in the core of the molecule and electron donor units, (A is phenyl) form the first branching point of a first generation biphenyl dendron with C as 2-ethylhexyloxy.
2.10
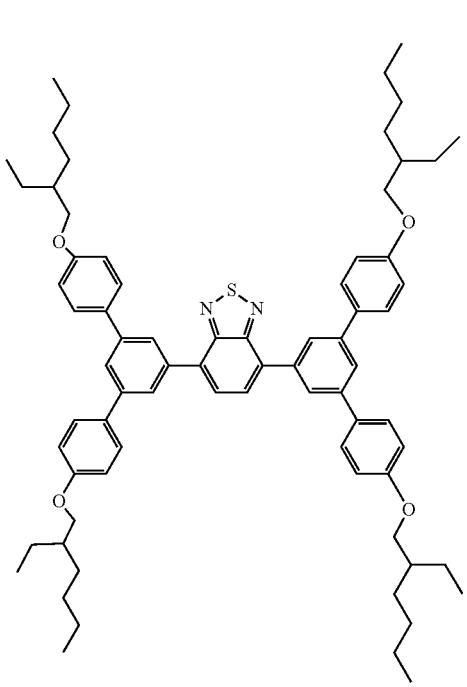
G1-BT-G1
2.12
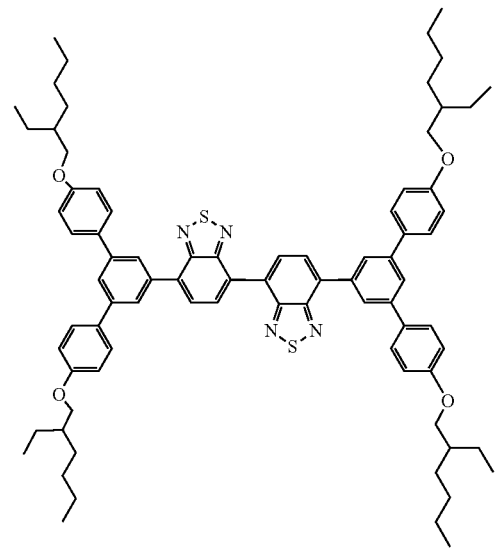
G1-BTBT-G1
The following are further additional examples of dendrimers.
WJ05-106
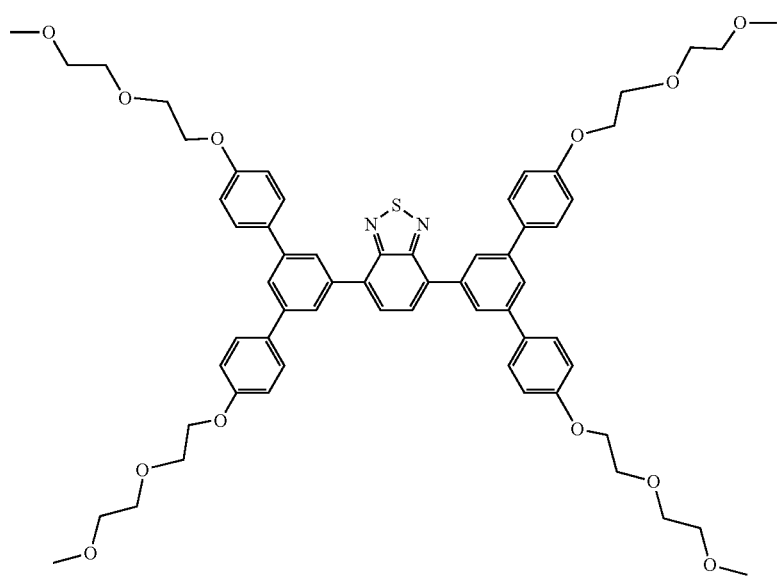

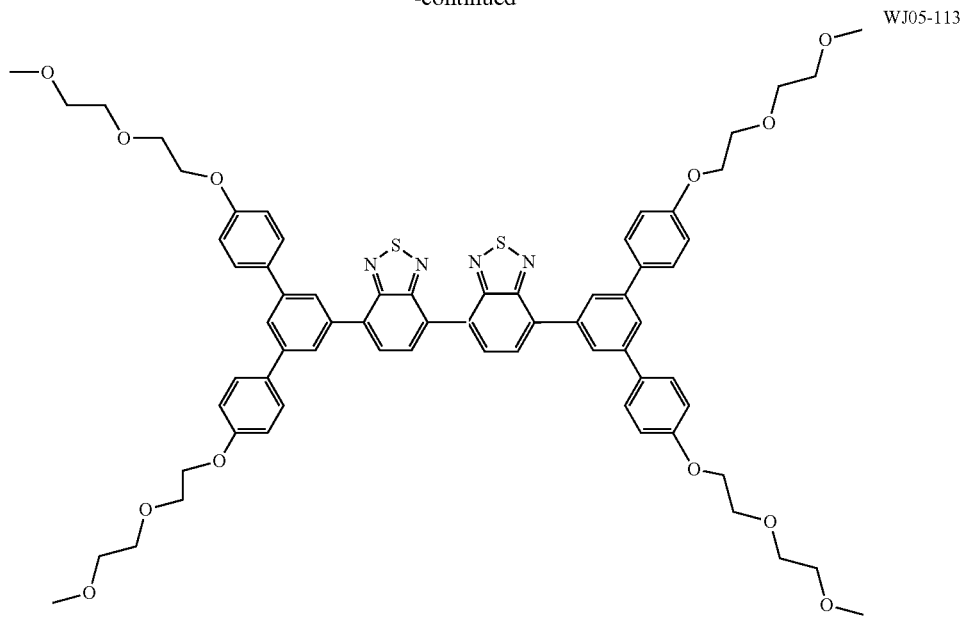

In some embodiments, the sensing compound is K12. When the detection method involves detection in an aqueous phase, in some embodiments the sensing compound is K12. In some embodiments, the sensing compound is not JED.

In some embodiments, a sensing compound is novel. Accordingly, the present invention also encompasses novel sensing compounds as described herein, for example AL03-77; AL03-79; AL03-56; AL03-28; AL03-100; AL03-102; AL03-96; AL03-09; WJ05-106; and WJ05-113. The present invention also encompasses the novel sensing compound WJ07-24.

The photoexcited sensing compound used in the present invention interacts with a narcotic thereby causing a fluorescence quenching effect. The interaction can take place at room temperature and pressure, which simplifies design of a sensing device in which the sensing compound/optical sensing element is used. However, this is not essential and it is possible that the interaction takes place at elevated temperature and the device designed accordingly to facilitate this. For example, the device may require some form of heating means to raise the temperature of the optical sensing element to provide a stable testing temperature independent of the environment or change the absorption/desorption kinetics.

The mechanism that causes fluorescence quenching of the photoexcited sensing compound when exposed to the narcotic is photo-induced electron transfer (PET). That is, on excitation of the sensing compound an electron is transferred from the analyte to the sensing molecule leading to a pathway by which the excited state can then undergo non-radiative decay. For this to take place the energy of the highest occupied molecular orbital (HOMO) or ionization potential of the sensing compound must be such that on excitation the exciton can oxidise the narcotic. The fluorescence quenching effect when the narcotic interacts with photoexcited sensing compound may be transient. The optical sensing element may therefore be reusable.

In an embodiment of the invention in the optical sensing element the sensing compound is provided as a thin film coating on a solid transparent substrate. The term "transparent" refers to the ability of the substrate to allow transmission of electromagnetic radiation used for photoexcitation of the sensing compound. In this embodiment the optical sensing element is therefore a solid-state system. The sensing compound will typically be provided as a continuous layer (coating) on the transparent substrate. To produce the coating the sensing compound may be dissolved in a solvent and applied to the substrate using conventional means for coating. The solvent is then removed leaving the sensing compound as a coating on the substrate. Examples of suitable solvents that may be useful in the practice of the invention include toluene, chlorinated solvents such as dichloromethane and chloroform, acetone, ethanol, methanol, iso-propanol, tert-butanol, methoxyethanol, tetrahydrofuran (THF), N,N-dimethylformamide (DMF), dimethyl sulfoxide (DMSO), 1,3-dioxane and 1,4-dioxane, or mixture thereof.

Typically the film coating will have a thickness of 100 nm, or less. In some embodiments, the film coating has a thickness of 20 nm to 100 nm or 50 nm to 100 nm, for example 50 nm to 80 nm. In some embodiments, the coating is a thin coating of 20 nm to 50 nm, for example 20 nm to 30 nm, or 25 nm to 35 nm.

In the optical sensing element, a polymer may also be employed with the sensing compound to form the coating. This may be appropriate in scenarios that require large-area and/or thick coatings or to change the polarity of the film. Examples of suitable polymers that may be useful in practice of the invention include polyethylene oxide (PEO) and cellulose acetate. Methods of coating a substrate are well known, and will depend on the shape, configuration and/or chemical composition of the substrate.

The minimum amount of sensing compound provided in the coating will be that required to produce a detectable fluorescent emission when excited and a detectable fluorescence quenching when the photoexcited sensing compound is exposed to a narcotic.

The amount of sensing compound included in the coating may be determined experimentally. The thickness of the sensing film will determine how quickly signal saturation is reached, with thicker films taking longer and potentially allowing for multiple detection events. When the response from the interaction with the narcotic is reversible the films can be reused and the thickness only needs to be such that a measurable change in the fluorescence is observable in each sensing event.

The substrate may take a variety of forms, and may depend on the phase employed in the method of detection. Methods of detection include those where the analyte is analysed in the vapour phase. In some methods, the analyte is in solution. It will be appreciated that the nature of the substrate should be compatible with the detection technique with regard to, for example, resistance to solubility, chemical compatibility with sensing compound and/or degradation by heat, light or chemical reaction. For example, a substrate may be a glass such as borosilicate glass or fused silica.

For vapour phase detection, the substrate may take the form of, for example, a tube or a surface in an enclosed channel with the sensing compound provided as a coating on an internal surface of the tube or surface in the channel. In this case a sample to be tested is provided to the interior of the tube or enclosed channel for contacting where it will come into contact with the sensing compound. Where the substrate is a tube it may be a capillary tube made of a glass, such as a borosilicate glass or silica. Typically the capillary tube will have an internal diameter of up to 1 mm. The length of the capillary tube is usually no more than 100 mm. Capillary tubes useful in the invention are commercially available and may be cut to an appropriate length.

For solution phase detection, such as aqueous phase detection, the substrate may take the form of, for example, a tube or a surface in an enclosed channel with the sensing compound provided as a coating on an internal surface of the tube or surface in the channel. In this case a sample to be tested is provided to the interior of the tube or enclosed channel for contacting where it will come into contact with the sensing compound. Where the substrate is a tube it may be a made of a glass, such as a borosilicate glass or fused silica. The length of the capillary tube is usually no more than 100 mm. Tubes useful in the invention are commercially available and may be cut to an appropriate length.

In one embodiment for solution phase detection, the sensing compound may be provided as a coating on a planar substrate such a slide of borosilicate glass or fused silica. The slide is placed in contact with the solution to be tested. Typically the slide will be of suitable dimension to fit in a container such as a vial or cuvette where it can contact the analyte solution to be tested. Typically the cuvette will be of suitable dimensions to fit in a conventional spectrometer.

A desirable property of the optical sensing element of the invention is that it is non-scattering when irradiated, as takes place during the detection process. Preferred substrates are transparent. However, in certain applications and configurations reflective substrates may also be useful.

In some embodiments, the response from the interaction of the sensing compound with the narcotic is reversible. Reversibility typically occurs when the sensing element recovers its original detection properties after the analyte is removed. In such circumstances, the sensing element may be used again. It will be appreciated that an activator may be required to promote reversibility. Reversibility may be encouraged by heating the sensing element.

The present invention uses an irradiation source for irradiating the optical sensing element with stimulating radiation in order to photoexcite the sensing compound prior to contacting with a sample that may include a narcotic to be detected. Generally the exciting radiation is in the UV or near UV-deep blue or blue register.

A detector is used for measuring any luminescent response (quenching) of the optical sensing element when photoexcited and after exposure to a sample. It is envisaged that the luminescent response will be measured with a broadband detector such as a photodiode. To maximize sensitivity an amplified detector such as an avalanche photodiode or photomultiplier tube could be used. Alternatively, a spectrally resolved detector such as CCD spectrograph may be used to resolve changes in the luminescence shape and intensity. In addition, a long-pass or band-pass optical filter may be included between the sensor and the detector to block the excitation wavelength from reaching the detector. The detection will include some means for relating to an operator the luminescence measured by the detector. This may involve some form of signal, for example a signal that is communicated visually, audibly or stimulatory (for example by vibration).

The device of the invention will also include a means for delivering a sample to be analysed for contacting with the (photoexcited) optical sensing element. FIG. 1 depicts components that may be present in a device useful for implementing the present invention.

For vapour phase detection, the sample will be gaseous. Typically, this means a fan or blower or pump coupled with a flow meter will be needed to continuously draw the sample into contact with the optical sensing element. For solution phase detection, the sample will be in solution and typically the sample may be drawn into contact with the sensing element using a pump.

In some embodiments, for solution phase detection, the optical sensing element is contacted by a solution of the analyte. This may be achieved for example by placing the sensing element in contact with the analyte solution, for example in a container such as a vial or cuvette.

Where the sample to be tested comprises a narcotic in the form of an acid addition salt, such as a hydrochloride, it may be necessary or desirable under certain circumstances to convert the acid addition salt to its free base prior to analysis. Accordingly, in the methods of the invention, a sample to be analysed may be processed so that narcotics present in the sample are converted to their free base form prior to contacting the sample with the optical sensing element. A sensing device of the invention may comprise means for converting any narcotic present in the sample to be tested to its corresponding free base. In this respect, the sensing device may therefore additionally include a component to prepare the sample, for example to convert any narcotic acid addition salt present in the sample to its free base. For example, such a component for preparing the sample may be comprised in the means for delivering the sample for contacting with the optical sensing element. It will also be appreciated that a component to prepare the sample may form a separate component to the means for delivering the sample.

The analyte solution may be an aqueous solution. In some embodiments, it may be beneficial to use a buffered solution. An aqueous solution may also be in the form of waste water, for example from drains, sewage and the like. It will also be appreciated that the aqueous solution may be a physiological fluid such as, for example, blood, saliva or urine, thus facilitating detection of drug abuse in an individual.

In some embodiments, for example in solution phase, the degree of quenching may be quantitative when compared with the concentration of narcotic present in the sample. This can provide access to a method of determining the amount of narcotic present.

Embodiments of the present invention are illustrated with reference to the following non-limiting examples.

EXAMPLES

Example 1: Synthesis of Sensing Materials

The sensing materials FI-BT; FI-BT-FI; FI-BTBT-FI; K12; K12-Th; K12b; HBP(BT-FI) 6; Ad (BT-FI) 4; K12-3; K12-6; G1-BT-G1; G1-BTBT-G1; 4.24; and 4.7 as depicted above can be prepared following the methods described in the PHD Thesis of Dr Ke Gui [Gui, Ke (2012) "Novel materials for bulk heterojunction thin film organic photovoltaic devices-research and application", School of Chemistry and Molecular Biosciences, The University of Queensland, Australia, doi.org/10.14264/uql.2017.795], which is viewable in UQ eSpace (https://espace.library.uq.edu.au/view/UQ: 282067). The contents of this thesis are incorporated herein by reference in their entirety. The synthesis of JED can be found in J. E. Donaghey, A. Armin, Dani M. Stoltzfus, P. L. Burn, P. Meredith, "Dielectric constant enhancement of non-fullerene acceptors via side-chain modification", Chem. Comm., DOI: 10.1039/c6cc90512a. Additional compounds may be prepared according to known routes, or in accordance with the synthetic routes described below.

Example 1a: Synthesis of AL03-77

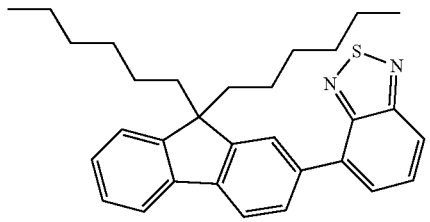 [SMILES: CCCCCCC1(CCCCCC)c2ccccc2-c2ccc(-c3cccc4nsnc34)cc21]

A mixture of (9,9-di-n-hexyl-9H-fluoren-2-yl) boronic acid [J. Am. Chem. Soc., 2004, 126, 13695-13702] (915 mg, 2.42 mmol), 4-bromobenzo[c][1,2,5]thiadiazole [J. Phys. Chem. B, 2012, 116, 7259-7268] (434 mg, 2.02 mmol), and potassium carbonate (1.20 g, 8.70 mmol) in toluene (20 mL), ethanol (8 mL), and water (12 mL) was placed under vacuum until boiling and backfilled with argon six times. Tetrakis(triphenylphosphine)-palladium (0) (100 mg, 0.087 mmol) was added and the solution heated in an oil bath held at 100° C. overnight under a blanket of argon. The solution when then cooled, diluted with water (90 mL), diethyl ether (90 mL), brine (60 mL), and the layers separated. The aqueous solution was extracted with diethyl ether (3×60 mL) and the combined organic extracts were washed with water (2×60 mL), brine (60 mL), dried over anhydrous magnesium sulphate, filtered on a silica plug, and the solvent removed in vacuo. The crude residue was purified by column chromatography over silica using a dichloromethane:light petroleum mixture (0:1 to 1:10) as eluent to afford AL03-77 as yellow/green oil after removal of the solvent (751 mg, 79%). $^1$H NMR (500 MHZ, CDCl3) δ:0.66-0.83 (10H, m, HexH), 1.00-1.12 (12H, m, HexH), 1.95-2.09 (4H, m, HexH), 7.31-7.40 (3H, m, FlH), 7.71 (1H, dd, J=8.5, 8.5 Hz, BTH), 7.76 (2H, dd, J=1.0, 7.0 Hz, FlH), 7.85 (1H, dd, J=0.5, 8.0 Hz, BTH), 7.90 (1H, d, J=0.5 Hz, BTH), 7.97 (1H, dd, J=1.5, 8.0 Hz, FlH), 8.00 (1H, dd, J=1.0, 8.5 Hz, FlH). HRMS (ESI-MS) for $C_{31}H_{36}N_2S$ [M+Na]$^+$ Calcd: 491.2491 (100%), 492.2522 (34%), 493.2511 (10%). Found: 491.2491 (100%), 492.2500 (40%), 493.2480 (12%).

Example 1b: Synthesis of AL03-79

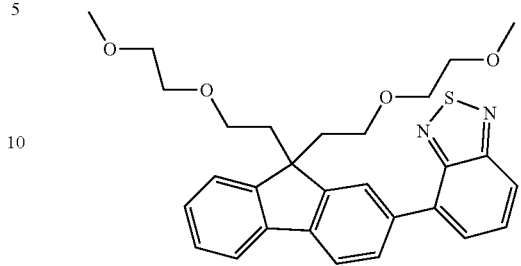

A mixture of [9,9-bis(2-{2-methoxyethoxy}ethyl)-9H-fluoren-2-yl]boronic acid [J. Mater. Chem. C, 2015, 3, 9412-9424] (92 mg, 0.222 mmol), 4-bromobenzo[c][1,2,5]thiadiazole [J. Phys. Chem. B, 2012, 116, 7259-7268] (38 mg, 0.177 mmol), and potassium carbonate (194 mg, 3.46 mmol) in toluene (10 mL), ethanol (1 mL), and water (2 mL) was placed under vacuum until boiling and backfilled with argon three times. Tetrakis(triphenylphosphine) palladium (0) (10 mg, 0.009 mmol) was added and the solution heated in an oil bath held at 110° C. overnight under a blanket of argon. The solution when then cooled, diluted with water (20 mL), ethyl acetate (20 mL), and the layers separated. The aqueous solution was extracted with ethyl acetate (3×20 mL), and the combined organic extracts washed with brine (20 mL), dried over anhydrous sodium sulphate, filtered, and the solvent removed in vacuo. The crude residue was purified by column chromatography over silica using an ethyl acetate:light petroleum mixture (1:3) as eluent followed by a dichloromethane:diethyl ether mixture (1:1) to afford AL03-79 as a yellow/green oil after removal of the solvent (48 mg, 52%). 1H NMR (500 MHZ, CDCl3) δ:2.42-2.55 (4H, m, GlH), 2.80-2.93 (4H, m, GlH), 3.20-3.23 (4H, m, GlH), 3.25 (6H, s, GlH), 3.27-3.32 (4H, m, GlH), 7.32-7.40 (2H, m, FlH), 7.45-7.48 (1H, m, FlH), 7.72 (1H, dd, J=7.0, 8.5 Hz, BTH), 7.74-7.76 (1H, m, FlH), 7.78 (1H, dd, J=1.0, 7.0 Hz, BTH), 7.84 (1H, dd, J=0.5, 8.0 Hz, BTH), 7.97-7.99 (1H, m, FlH), 8.00 (1H, d, J=1.0 Hz, FlH), 8.02-8.03 (1H, m, FlH). HRMS (ESI-MS) for $C_{29}H_{32}N_2O_4S$ [M+Na]$^+$ Calcd: 527.1975 (100%), 528.2009 (31%). Found: 527.1997 (100%), 528.2021 (34%).

Example 1c: AL03-56

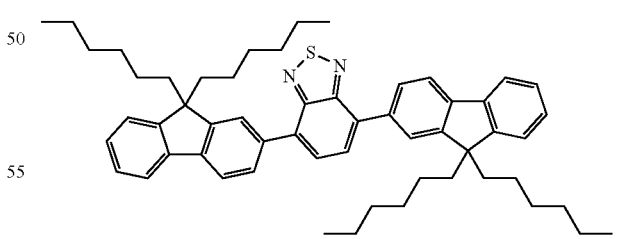

A mixture of (9,9-di-n-hexyl-9H-fluoren-2-yl) boronic acid [J. Am. Chem. Soc., 2004, 126, 13695-13702] (300 mg, 0.799 mmol), 4,7-dibromobenzo[1,2,5]thiadiazole [Polymer, 2010, 51, 6123-6131] (109 mg, 0.372 mmol), and potassium carbonate (550 mg, 3.99 mmol) in ethanol (3 mL), toluene (8 mL), and water (5 mL) was placed under vacuum until boiling and backfilled with argon six times. Tetrakis(triphenylphosphine)-palladium (0) (30 mg, 0.026 mmol) was added and the solution heated in an oil bath held at 110° C. overnight under a blanket of argon. The solution when then cooled, diluted with water (30 mL), diethyl ether (50 mL), and the layers separated. The aqueous solution was extracted with diethyl ether (3×30 mL), light petroleum (2×30 mL), and the combined organic extracts washed with water (50 mL), brine (50 mL), dried over anhydrous magnesium sulphate, filtered on a silica plug, and the solvent removed in vacuo. The crude material was initially purified by column chromatography over silica using a dichloromethane:light petroleum mixture (0:1 to 1:10) as eluent to afford a yellow solid. The solid was then recrystallised from dichloromethane and methanol to afford AL03-56 as a yellow solid (134 mg, 45%). 1H NMR (500 MHZ, CDCl3) δ:0.68-0.86 (20H, m, HexH), 1.02-1.19 (24H, m, HexH), 1.96-2.12 (8H, m, HexH), 7.31-7.41 (6H, m, FlH), 7.78 (2H, dd, J=1.0, 6.5 Hz, FlH), 7.87 (2H, d, J=8.0 Hz, FlH), 7.89 (2H, s, BTH), 7.96 (2H, d, J=1.5 Hz, FlH), 8.02 (2H, dd, J=1.5, 8.0 Hz, FlH). HRMS (ESI-MS) for $C_{56}H_{68}N_2S$ $[M+Na]^+$ Calcd: 823.4995 (100%), 824.5027 (57%), 825.5043 (23%). Found: 823.5024 (100%), 824.5030 (64%), 825.5029 (26%).

Example 1d: AL03-28

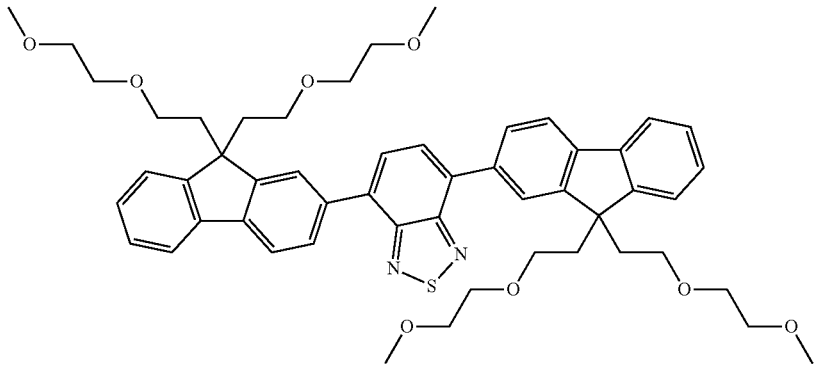

A mixture of [9,9-bis(2-{2-methoxyethoxy}ethyl)-9H-fluoren-2-yl]boronic acid [J. Mater. Chem. C, 2015, 3, 9412-9424] (1.27 g, 2.83 mmol), 4,7-dibromobenzo[1,2,5]thiadiazole [Polymer, 2010, 51, 6123-6131] (362 mg, 1.23 mmol), and potassium carbonate (2.03 g, 14.7 mmol) in ethanol (10 mL), toluene (35 mL), and water (7 mL) was placed under vacuum until boiling and backfilled with argon six times. Tetrakis(triphenylphosphine) palladium (0) (155 mg, 0.134 mmol) was added and the solution heated in an oil bath held at 105° C. overnight under a blanket of argon. The solution when then cooled, diluted with water (25 mL), ethyl acetate (25 mL), and the layers separated. The aqueous solution was extracted with ethyl acetate (3×50 mL), and the combined organic extracts washed with water (2×50 mL), brine (50 mL), dried over anhydrous sodium sulphate, filtered, and the solvent removed in vacuo. The crude material was initially purified by column chromatography over silica using an ethyl acetate:light petroleum mixture (3:1) as eluent to afford a yellow solid. The solid was then recrystallised from dichloromethane, diethyl ether, and n-hexane to afford AL03-28 as a yellow solid (970 mg, 90%). 1H NMR (500 MHZ, CDCl3) &: 2.43-2.60 (8H, m, GlH), 2.82-3.00 (8H, m, GlH), 3.20-3.37 (28H, m, GlH), 7.33-7.42 (4H, m, FlH), 7.46-7.51 (2H, m, FlH), 7.75-7.79 (2H, m, FlH), 7.87 (2H, d, J=8.0 Hz, FlH), 7.90 (2H, s, BTH), 8.05 (2H, d, J=1.5 Hz, FlH), 8.07 (2H, dd, J=1.5, 8.0 Hz, FlH). HRMS (ESI-MS) for $C_{52}H_{60}N_2O_8S$ $[M+Na]^+$ Calcd: 895.3963 (100%), 896.3997 (54%), 897.4005 (23%). Found: 895.3952 (100%), 896.3931 (63%), 897.3899 (29%).

Example 1e: AL03-100

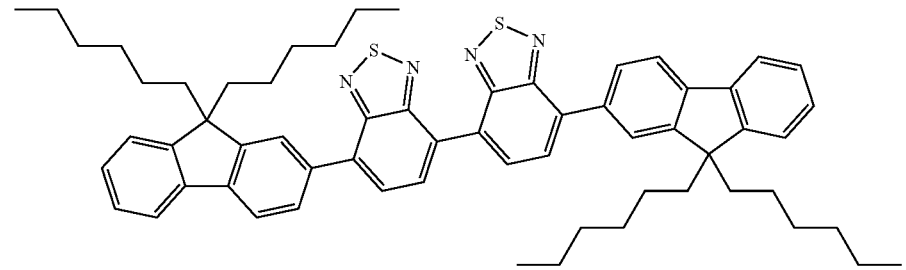 [SMILES: CCCCCCC1(CCCCCC)c2ccccc2-c2ccc(-c3ccc(-c4ccc(-c5ccc6c(c5)C(CCCCCC)(CCCCCC)c5ccccc5-6)c5nsnc45)c4nsnc34)cc21]

A mixture of (9,9-di-n-hexyl-9H-fluoren-2-yl) boronic acid [J. Am. Chem. Soc., 2004, 126, 13695-13702] (250 mg, 0.661 mmol), 7,7'-dibromo-4,4'-bibenzo[c][1,2,5]thiadiazole [Org. Lett., 2008, 10, 5533-5536] (100 mg, 0.234 mmol), and potassium carbonate (400 mg, 2.90 mmol) in toluene (10 mL), ethanol (4 mL), and water (6 mL) was placed under vacuum until boiling and backfilled with argon six times. Tetrakis(triphenylphosphine) palladium (0) (15 mg, 0.013 mmol) was added and the solution heated in an oil bath held at 110° C. for 3 days, under a blanket of argon, in the absence of light. The solution when then cooled, diluted with water (20 mL), diethyl ether (30 mL), and the layers separated. The aqueous solution was extracted with diethyl ether (4×25 mL), and the combined organic extracts washed with brine (30 mL), dried over anhydrous magnesium sulphate, filtered through a silica plug, and the solvent removed in vacuo. The crude material was initially purified by column chromatography over silica using a dichloromethane:light petroleum mixture (3:10) as eluent to afford a yellow solid after removal of the solvent. The solid was recrystallised from dichloromethane and light petroleum to afford AL03-100 as a bright yellow solid (140 mg, 64%). $^1$H NMR (500 MHZ, CDCl3) δ:0.70-0.87 (20H, m, HexH), 1.03-1.21 (24H, m, HexH), 1.97-2.14 (8H, m, HexH), 7.33-7.42 (6H, m, FlH), 7.77-7.81 (2H, m, FlH), 7.90 (2H, d, J=8.0 Hz, FlH), 7.99 (2H, d, J=1.5 Hz, FlH), 8.01 (2H, d, J=7.5 Hz, BTH), 8.07 (2H, dd, J=1.5, 8.0 Hz, FlH), 8.49 (2H, d, J=7.5 Hz, BTH). HRMS (ESI-MS) for $C_{62}H_{70}N_4S_2$ [M]$^+$ Calcd: 934.5064 (100%), 935.5101 (95%), 936.5115 (51%), 937.5136 (19%). Found: 934.5034 (100%), 935.5068 (71%), 936.5072 (34%), 937.5076 (12%).

Example 1f: AL03-102

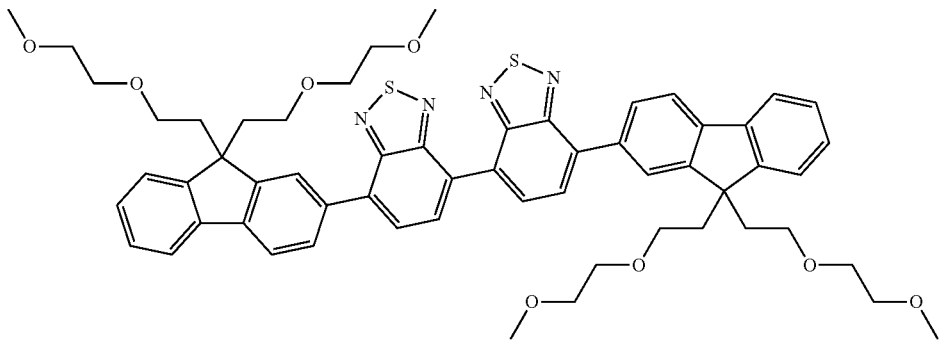

A mixture of [9,9-bis(2-{2-methoxyethoxy}ethyl)-9H-fluoren-2-yl]boronic acid [J. Mater. Chem. C, 2015, 3, 9412-9424] (240 mg, 0.580 mmol), 7,7'-dibromo-4,4'-bibenzo[c][1,2,5]thiadiazole [Org. Lett., 2008, 10, 5533-5536] (87 mg, 0.203 mmol), and potassium carbonate (350 mg, 2.54 mmol) in toluene (10 mL), ethanol (4 mL), and water (6 mL) was sparged with argon for 10 mins. Tetrakis(triphenylphosphine) palladium (0) (15 mg, 0.013 mmol) was added and the solution heated in an oil bath held at 110° C. for 2 days, under a blanket of argon, in the absence of light. The solution when then cooled, diluted with water (20 mL), diethyl ether (50 mL), and the layers separated. The aqueous solution was extracted with diethyl ether (5×50 mL), and the combined organic extracts washed with brine (2×50 mL), dried over anhydrous magnesium sulphate, filtered through a silica plug, and the solvent removed in vacuo. The crude material was initially purified by column chromatography over silica using diethyl ether as eluent followed by an ethyl acetate:toluene mixture (1:1) to afford AL03-102 as a red solid after removal of the solvent (54 mg, 26%). 1H NMR (500 MHz, CDCl$_3$) δ:2.44-2.59 (8H, m, GlH), 2.84-2.98 (8H, m, GlH), 3.19-3.37 (28H, m, GlH), 7.34-7.42 (4H, m, FlH), 7.49 (2H, dd, J=1.0, 6.5 Hz, FlH), 7.78 (2H, dd, J=1.0, 6.5 Hz, FlH), 7.89 (2H, d, J=8.0 Hz, BTH), 8.02 (2H, d, J=7.5 Hz, BTH), 8.09 (2H, d, J=1.0 Hz, BTH), 8.11 (2H, dd, J=1.5, 8.0 Hz, FlH), 8.49 (2H, d, J=7.5 Hz, FlH).

Example 1g: AL03-96

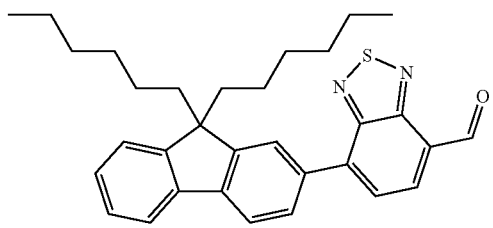 [SMILES: CCCCCCC1(CCCCCC)c2ccccc2-c2ccc(-c3ccc(C=O)c4nsnc34)cc21]

A mixture of (9,9-di-n-hexyl-9H-fluoren-2-yl) boronic acid [J. Am. Chem. Soc., 2004, 126, 13695-13702] (500 mg, 1.32 mmol), 7-bromobenzo[c][1,2,5]thiadiazole-4-carbaldehyde [J. Am. Chem. Soc., 2004, 126, 13695-13702] (258 mg, 1.06 mmol), potassium carbonate (680 mg, 12.1 mmol) in toluene (10 mL), ethanol (4 mL), and water (6 mL) was sparged with argon for 10 mins. Tetrakis(triphenylphosphine) palladium (0) (60 mg, 0.052 mmol) was added and the solution heated in an oil bath held at 110° C. overnight under a blanket of argon. The solution when then cooled, diluted with water (100 mL), diethyl ether (100 mL), and the layers separated. The aqueous solution was extracted with diethyl ether (4×50 mL), and the combined organic extracts washed with water (2×50 mL), brine (50 mL), dried over anhydrous sodium sulphate, filtered, and the solvent removed in vacuo. The crude reside was initially purified by column chromatography over silica using a dichloromethane:light petroleum mixture (3:10 to 4:5) as eluent to afford an orange solid. The solid was recrystallised from dichloromethane and methanol to afford AL03-96 as a bright orange solid (445 mg, 84%). $^1$H NMR (500 MHz, CDCl$_3$) δ:0.66-0.81 (10H, m, HexH), 1.01-1.17 (12H, m, HexH), 1.96-2.12 (8H, m, HexH), 7.34-7.42 (3H, m, FlH), 7.76-7.81 (1H, m, FlH), 7.88 (1H, dd, J=0.5, 8.0 Hz, FlH), 7.96 (1H, dd, J=0.5, 7.5 Hz, BTH), 7.99 (1H, dd, J=0.5, 2.0 Hz, FlH), 8.03 (1H, dd, J=2.0, 8.0 Hz, FlH), 8.34 (1H, d, J=7.5 Hz, BTH), 10.81 (1H, s, CHO). HRMS (ESI-MS) for $C_{32}H_{36}N_2OS$ [M+Na]$^+$ Calcd: 497.2621 (100%), 498.2655 (35%). Found: 497.2604 (100%), 498.2634 (36%).

Example 1h: AL04-09

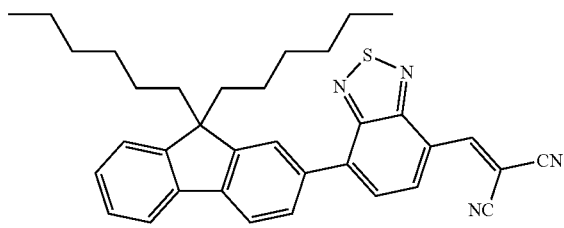 [SMILES: CCCCCCC1(CCCCCC)c2ccccc2-c2ccc(-c3ccc(C=C(C#N)C#N)c4nsnc34)cc21]

AL03-96 (443 mg, 0.893 mmol) and malononitrile (313 mg, 4.74 mmol) in anhydrous toluene (10 mL) was evacuated until boiling and backfilled with argon three times. Pyridine (0.60 mL) was added and the solution heated in an oil bath held at 70° C. for 2 h under a blanket of argon. The solution was cooled to room temperature and the solvent removed in vacuo. The crude material was initially purified by column chromatography over silica using a dichloromethane:light petroleum mixture (1:1) as eluent to afford a red solid after removal of the solvent. The solid was recrystallised from dichloromethane and methanol to afford AL04-09 as a bright red solid (384 mg, 79%). 1H NMR (500 MHZ, CDCl3) δ:0.66-0.82 (10H, m, HexH), 1.00-1.17 (12H, m, HexH), 1.96-2.12 (4H, m, HexH), 7.35-7.42 (3H, m, FlH), 7.76-7.81 (1H, m, FlH), 7.89 (1H, dd, J=0.5, 7.5 Hz, FlH), 8.00 (1H, dd, J=0.5, 7.5 Hz, BTH), 8.02 (1H, dd, J=0.5, 2.0 Hz, FlH), 8.07 (1H, dd, J=1.5, 8.0 Hz, FlH), 8.84 (1H, dd, J=0.5, 7.5 Hz, BTH), 8.88 (1H, s, vinylH). Anal. Calc. for $C_{35}H_{36}N_4S$: C, 77.2; H, 6.7; N, 10.3; S, 5.9. Found: C, 77.4; H, 6.7; N, 10.2; S, 5.7.

Example 1i: WJ05-106

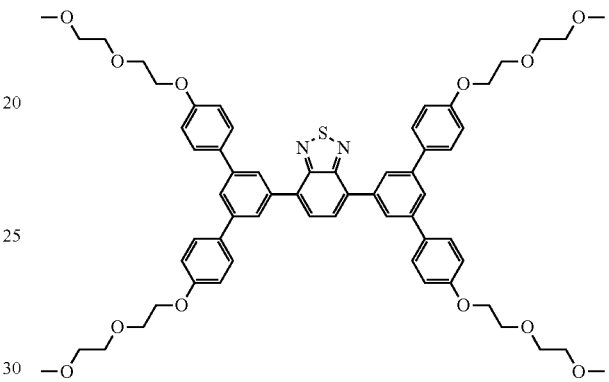

A mixture of 2-[4,4"-bis(2-{2-methoxyethoxy}ethoxy]-[1,1': 3',1"-terphenyl]-5'-yl)-4,4,5,5-tetramethyl-1,3,2-dioxaborolane [J. Mater. Chem. C, 2015, 3, 9412-9424] (199 mg, 0.334 mmol) and 4,7-dibromobenzo[1,2,5]thiadiazole [Polymer, 2010, 51, 6123-6131] (44 mg, 0.150 mmol) in potassium carbonate (2M, 0.3 mL), toluene (1.4 mL), and t-BuOH (0.2 mL) was subjected to two freeze-pump-thaw cycles with back filling with argon. Tetrakis(triphenylphosphine) palladium (0) (20 mg, 0.017 mmol) was added and the solution heated in an oil bath held at 100° C. for 2 days, under a blanket of argon, in the absence of light. The solution was cooled and diluted with dichloromethane (10 mL), diethyl ether (20 mL) and the layers separated. The aqueous solution was extracted with dichloromethane (2×10 mL) and the combined organic extracts washed dried on anhydrous sodium sulphate, filtered, and the solvent removed in vacuo. The crude residue was initially purified by column chromatography over silica using a diethyl ether:light petroleum mixture (1:1 to 1:0) as eluent followed by a methanol:ethyl acetate mixture (1:19) to afford WJ05-106 as a yellow/green solid after removal of the solvent (mg, 72%). $^1$H NMR (300 MHZ, CDCl3) δ:3.41 (12H, s, GlH), 3.56-3.65 (8H, m, GlH), 3.72-3.79 (8H, m, GlH), 3.91 (8H, t, J=5.0 Hz, GlH), 4.23 (8H, t, J=5.0 Hz, GlH), 6.99-7.11 (8H, m, ArH), 7.64-7.73 (8H, m, ArH), 7.82 (2H, t, J=1.5 Hz, ArH), 7.92 (2H, s, BTH), 8.09 (4H, d, J=1.5 Hz, ArH). LRMS (ESI-MS) for $C_{62}H_{68}N_2O_{12}S$ [M]$_+$ Calcd: 1064.45 (100.0%), 1065.45 (70%), 1066.46 (31%), 1067.46 (10%). Found: 1064.05 (51%), 1065.04 (100%), 1066.00 (83%), 1067.02 (26%).

Example 1j: WJ05-113

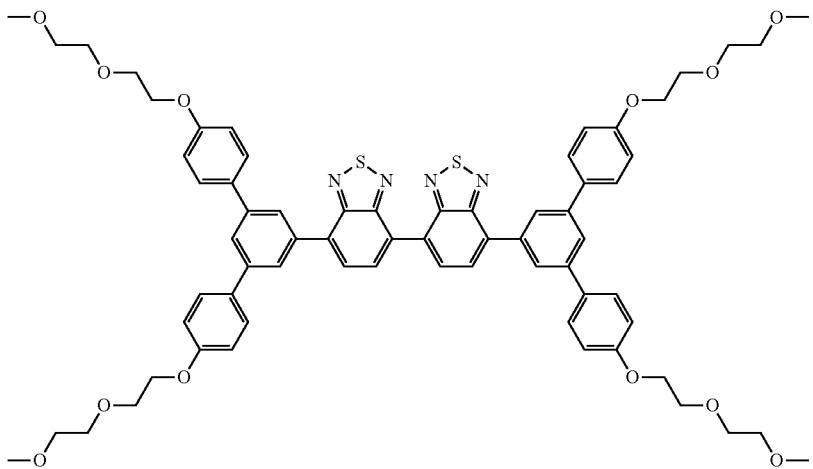

A mixture of 2-[4,4''-bis(2-{2-methoxyethoxy}ethoxy)-[1,1': 3',1''-terphenyl]-5'-yl)-4,4,5,5-tetramethyl-1,3,2-dioxaborolane [J. Mater. Chem. C, 2015, 3, 9412-9424] (152 mg, 0.257 mmol) and 7,7'-dibromo-4,4'-bibenzo[c][1,2,5]thiadiazole [Org. Lett., 2008, 10, 5533-5536] (49 mg, 0.114 mmol) in potassium carbonate (2M, 0.3 mL), toluene (1.3 mL), and r-butanol (0.2 mL) was subjected to three freeze-pump-thaw cycles with back filling with argon. Tetrakis (triphenylphosphine) palladium (0) (16 mg, 0.014 mmol) was added and the solution heated in an oil bath held at 100° C. for 3 days, under a blanket of argon, in the absence of light. The solution was cooled and diluted with dichloromethane (10 mL), water (10 mL) and the layers separated. The organic layer was washed with water (3×10 mL), dried on anhydrous sodium sulphate, and the solvent removed in vacuo. The crude residue was initially purified by column chromatography over silica using a diethyl ether:ethyl acetate mixture (1:1 to 0:1) as eluent followed by a methanol:ethyl acetate mixture (1:14) to afford a yellow solid removal of the solvent. The solid was reprecipitated from dichloromethane and methanol to afford WJ05-113 as a bright yellow solid (53 mg, 39%). 1H NMR (300 MHz, CDCl3) &: 3.42 (12H, s, GIH), 3.58-3.65 (8H, m, GIH), 3.73-3.80 (8H, m, GIH), 3.92 (8H, t, J=5.0 Hz, GIH), 4.23 (8H, t, J=5.0 Hz, GIH), 7.00-7.11 (8H, m, ArH), 7.64-7.73 (8H, m, ArH), 7.84 (2H, t, J=1.5 Hz, ArH), 8.04 (2H, d, J=7.0 Hz, BTH), 8.13 (4H, d, J=1.5 Hz, ArH), 8.49 (2H, d, J=7.0 Hz, BTH). LRMS (ESI-MS) for $C_{68}H_{70}N_4O_{12}S_2$ [M]$^+$ Calcd: 1199.45 (100.0%), 1200.45 (78%), 1201.46 (41%), 1202.46 (17%). Found: 1199.10 (100%), 1200.04 (88%), 1201.05 (47%), 1202.13 (15%).

Example 1k: WJ07-24

WJ07-12

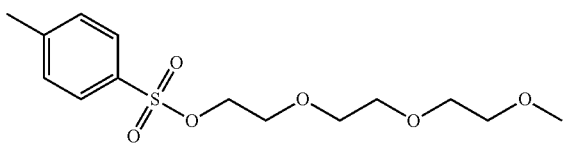

A mixture of 2-[2-(2-methoxyethoxy) ethoxy]ethan-1-ol (20.0 g, 122 mmol) and sodium hydroxide (7.89 g, 200 mmol) in tetrahydrofuran (150 mL) was cooled in an ice/water bath. A separate solution of p-toluenesulfonyl chloride (23.5 g, 124 mmol) in tetrahydrofuran (75 mL) was added dropwise over 1 hr. The resulting solution was stirred overnight, under a blanket of argon, in the absence of light. The solution was diluted with water (150 mL) and the layers separated. The aqueous solution was extracted with dichloromethane (3×20 mL) and the combined organic extracts dried over anhydrous sodium sulfate, filtered, and the solvent removed in vacuo to give WJ07-12 as a colourless oil (37.6 g, 97%). 1H NMR (300 MHz, CDCl3) δ:2.43 (s, 3H, Ar—CH3), 3.35 (s, 3H, GIH), 3.48-3.54 (m, 2H, GIH), 3.55-3.62 (m, 6H, GIH), 3.63-3.70 (m, 2H, GIH), 4.11-4.18 (m, 2H, GIH), 7.33 (d, 2H, J=8.0 Hz, ArH), 7.76 (2, 2H, J=8.0 Hz, ArH). LRMS (ESI-MS) for $C_{14}H_{22}O_6S$ [M+H]$^+$ Calcd: 319.1 (100%), 320.1 (16%). Found: 319.0 (100%), 319.9 (16%).

WJ07-15

WJ07-15

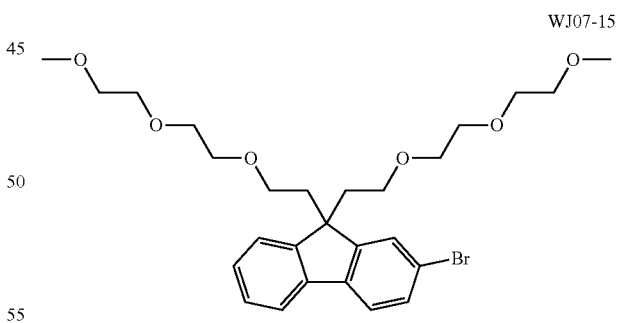

A mixture of WJ07-12 (22.8 g, 71.5 mmol) in anhydrous N,N-dimethylformamide (40 mL) was added dropwise to a solution of 2-bromo-9H-fluorene (7.0 g, 29 mmol) and potassium hydroxide (4.96 g, 88.4 mmol) in anhydrous N,N-dimethylformamide (40 mL) under a blanket of argon. The solution was stirred for 30 mins before being heated in an oil bath held at 60° C. overnight, under a blanket of argon, in the absence of light. The solution was allowed to cool to room temperature, diluted with diethyl ether (200 mL), water (150 mL), and the layers separated. The organic layer was washed with water (7×100 mL), dried over anhydrous sodium sulfate, filtered, and the solvent removed in vacuo. The crude residue was initially purified by column chromatography over silica using a diethyl ether:light petroleum mixture (1:1) as eluent followed by a diethyl ether:light petroleum mixture (1:4 to 1:5) to afford WJ07-15 as a yellow oil after removal of the solvent (9.4 g, 61%). $^1$H NMR (300 MHz, CDCl$_3$) δ:2.30-2.41 (m, 4H, GIH), 2.70-2.80 (m, 4H, GIH), 3.15-3.25 (m, 4H, GIH), 3.34 (s, 6H, GIH), 3.36-3.42 (m, 4H, GIH), 3.45-3.55 (m, 8H, GIH), 7.30-7.35 (m, 2H, FIH), 7.36-7.41 (m, 1H, FIH), 7.46 (dd, 1H, J=1.5 and 8.0 Hz, FIH), 7.53 (d, 1H, J=6.5 Hz, FIH), 7.55 (s, 1H, FIH), 7.61-7.67 (m, 1H, FIH). LRMS (ESI-MS) for C$_{27}$H$_{37}$BrO$_6$ [M+H]$^+$ Calcd: 537.2 (97%), 538.2 (29%), 539.2 (100%), 540.2 (29%). Found: 537.0 (97%), 538.0 (30%), 538.9 (100%), 539.8 (27%).

A mixture of WJ07-12 (4.34 g, 8.07 mmol), bis(pinacolato)diboron (2.48 g, 9.75 mmol), [1,1'-bis(diphenylphosphino) ferrocene]dichloropalladium (II) (330 mg, 0.451 mmol), and potassium acetate (2.40 g, 0.024 mmol) in anhydrous 1,4-dioxane (45 mL) was evacuated until boiling and backfilled with argon three times. The solution was heated in an oil bath held at 100° C. overnight, under a blanket of argon, in the absence of light. The solution was allowed to cool to room temperature, filtered through a plug of celite and the solvent removed in vacuo. The crude residue was purified by column chromatography over silica using a diethyl ether:light petroleum mixture (1:1 to 1:0) as eluent to afford WJ06-16 as a dark yellow oil after removal of the solvent (445 mg, 84%). $^1$H NMR (300 MHz, CDCl$_3$) δ:1.39 (s, 12H, CH$_3$), 2.31-2.50 (m, 4H, GIH), 2.62-2.79 (m, 4H, GIH), 3.19 (dd, 4H, J=3.5, 5.0 Hz, GIH), 3.33 (s, 6H, GIH), 3.36-3.41 (m, 4H, GIH), 3.44-3.53 (m, 8H, GIH), 7.28-7.37 (m, 2H, FIH), 7.38-7.45 (m, 1H, FIH), 7.67 (dd, 1H, J=1.0, 7.5 Hz, FIH), 7.69-7.73 (m, 2H, FIH), 7.80 (dd, 1H, J=1.0, 7.5 Hz, FIH), 7.83 (t, 1H, J=1.0 Hz, FIH). LRMS (ESI-MS) for C$_{33}$H$_{49}$BO$_8$ [M+H]$^+$ Calcd: 584.4 (22%), 585.4 (100%), 586.4 (35%). Found: 584.9 (100%), 585.9 (24%).

WJ07-16

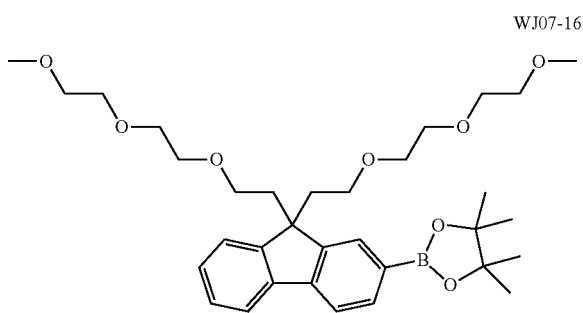

WJ07-17

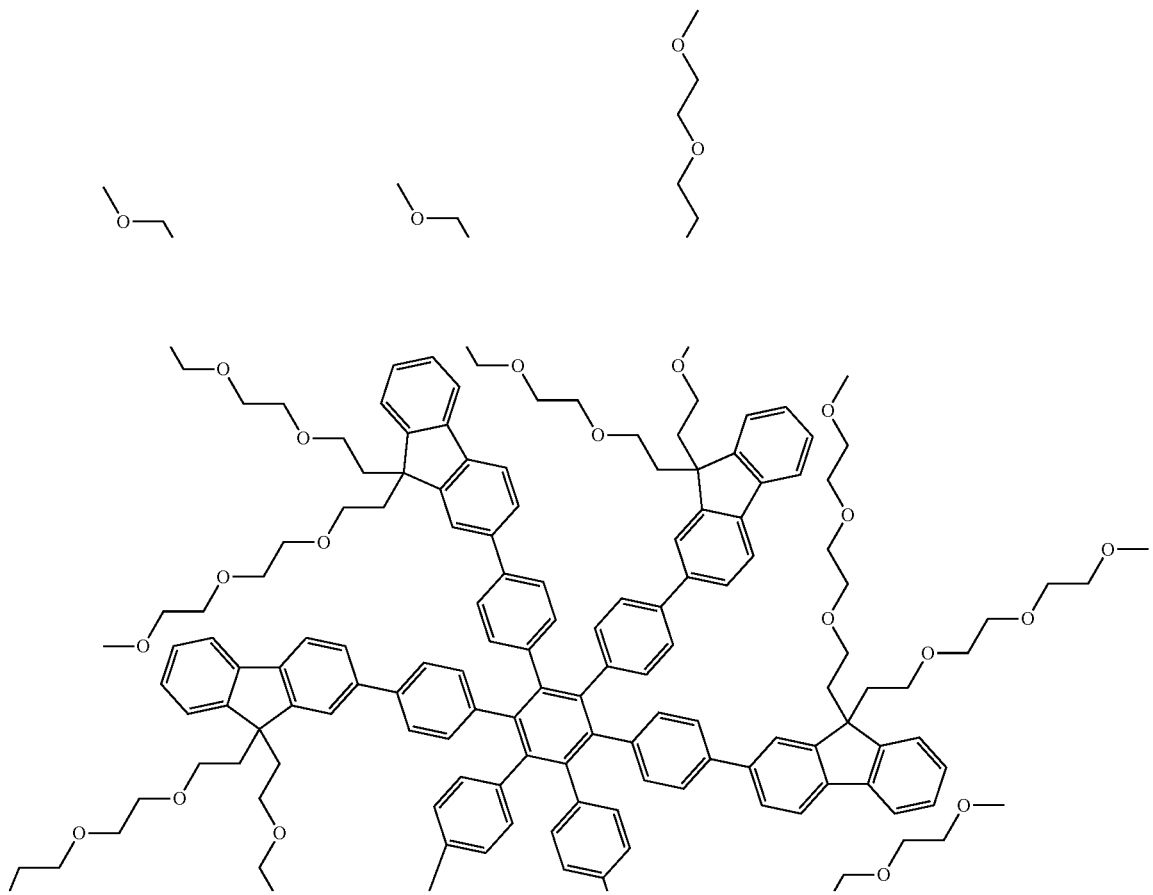

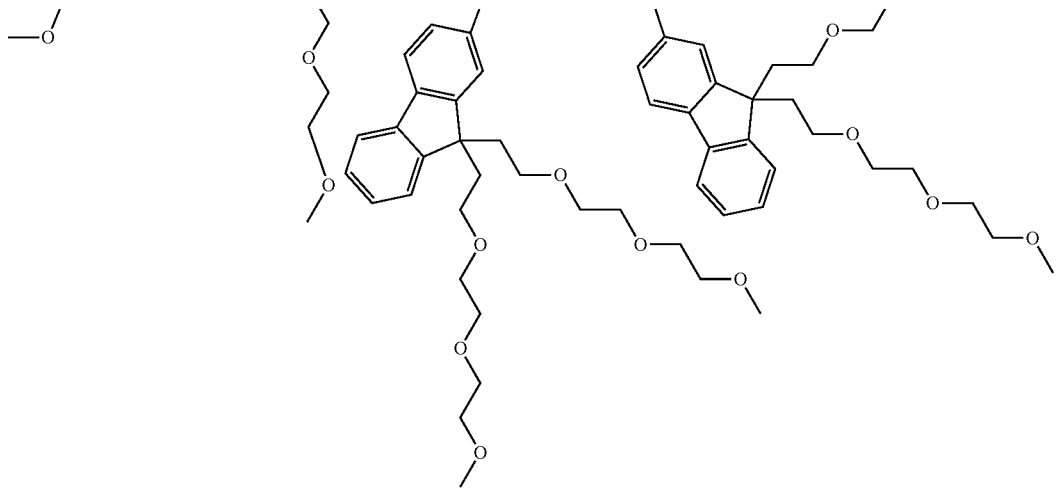

A mixture of hexa (4-iodophenyl)benzene [prepared according to the route of Kenji Kobayashi et. al., The Journal of Organic Chemistry, 2005 70, 749-752] (300 mg, 0.232 mmol) and WJ07-16 (1.18 g, 2.02 mmol) in toluene (14 mL) was subjected to three freeze-pump-thaw cycles followed by backfilling with argon. Tetraethylammonium hydroxide (4.6 mL, 20% aq.) was added and the solution again was subjected to one freeze-pump-thaw cycle with backfilling with argon. Tetrakis(triphenylphosphine) palladium (0) (32 mg, 0.03 mmol) was added and the solution heated in an oil bath held at 100° C. for overnight under argon in the absence of light. The solution was allowed to cool to room temperature, diluted with water (50 mL) and the layers separated. The aqueous solution was extracted with dichloromethane (3×20 mL), and the combined organic extracts were dried over anhydrous sodium sulfate, filtered followed by the solvent being removed in vacuo. The crude residue was purified by size exclusion chromatography (BioBeads) using tetrahydrofuran as eluent to afford WJ07-17 as a light yellow gum after removal of the solvent (646 mg, 85%). 1H NMR (500 MHz, CDCl$_3$) &: 2.33-2.37 (m, GIH), 2.71-2.81 (m, GIH), 3.14-3.20 (m, GIH), 3.28-3.36 (m, GIH), 3.39-3.49 (m, GIH), 7.02-7.20 (m, PhH), 7.24-7.45 (m, PhH and FIH), 7.52-7.56 (m, FIH), 7.62-7.66 (m, FIH); GPC: $\overline{M}_n$=2330, PDI=1.009.

WJ07-18

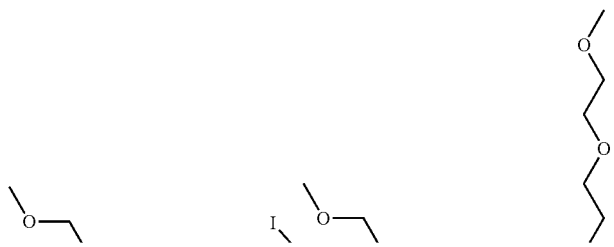

-continued
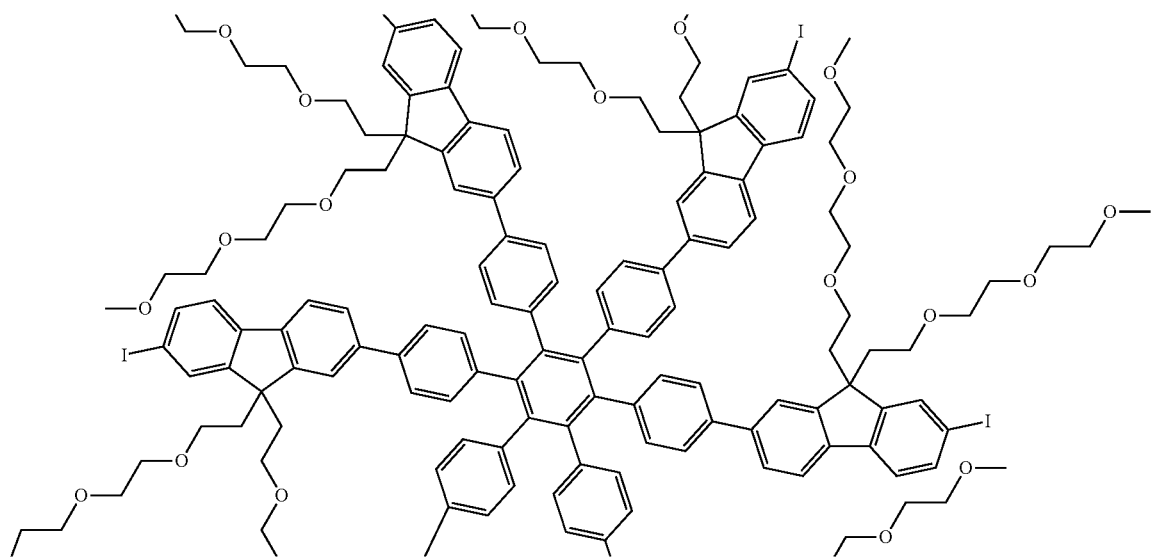
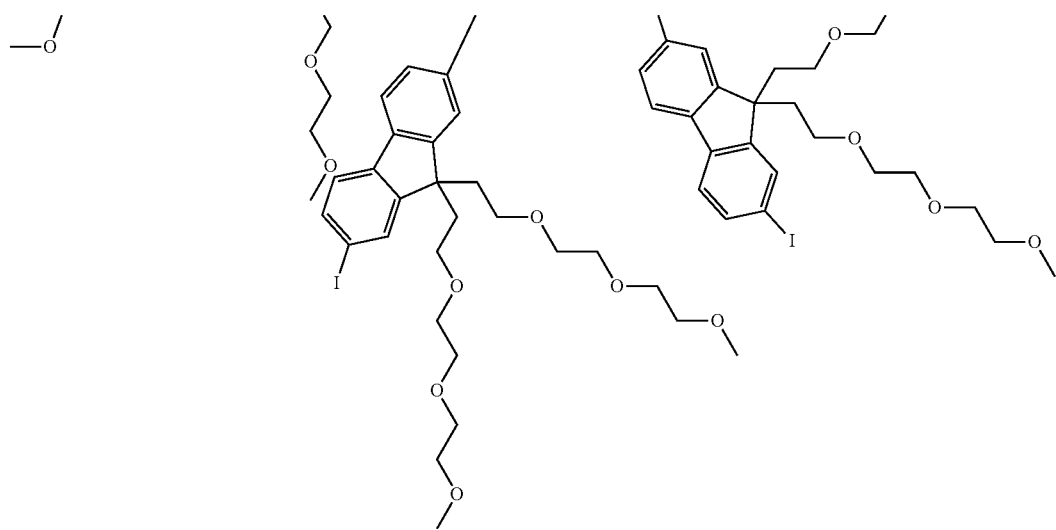

A mixture of WJ07-17 (490 mg, 0.150 mmol) and N-iodosuccinimide (542 mg, 2.41 mmol) in chloroform (13 mL) was evacuated until boiling and backfilled with argon three times. The solution was stirred for 30 mins, before trifluoroacetic acid (0.6 mL) was added and the solution heated in an oil bath held at 60° C. for 4 days, under a blanket of argon, in the absence of light. The solution was allowed to cool to room temperature, diluted with sodium metabisulfite (aq. sat. 60 mL), and stirred for 30 mins. The layers were separated and the organic layer washed with potassium carbonate (aq. sat. 60 mL), water (2×60 mL), dried over sodium sulfate, filtered, and the solvent removed in vacuo. The crude residue was purified by column chromatography over silica using a diethyl ether:methanol mixture (1:0 to 20:1) as eluent to afford WJ06-18 as a yellow gum after removal of the solvent (470 mg, 78%). $^1$H NMR (500 MHZ, $(CD_3)_2SO$) δ: 2.36-2.63 (br. m, GIH), 3.05-3.29 (br. m, GIH), 7.15-8.38 (br. m, PhH and FIH); GPC: $\overline{M}_n$=2563, PDI=1.005.

WJ07-20

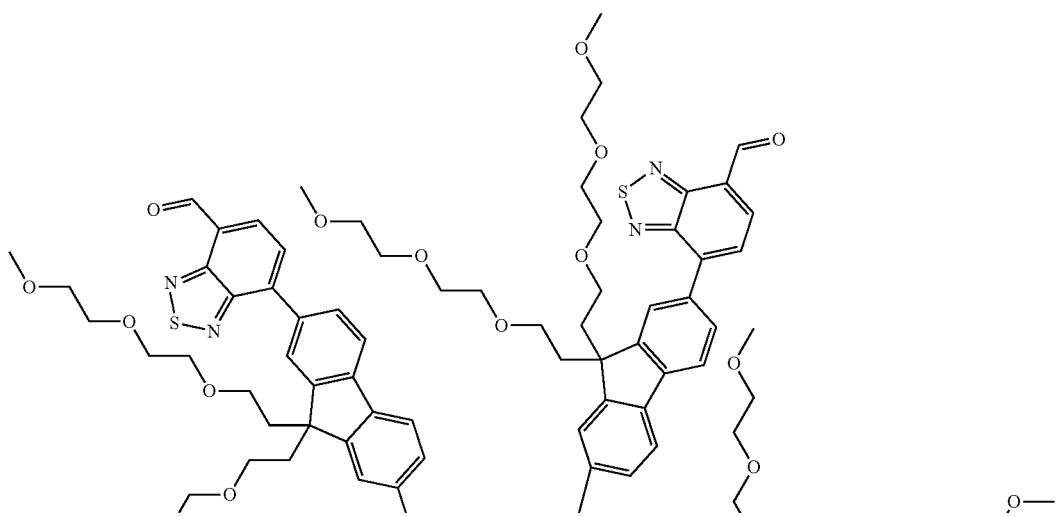

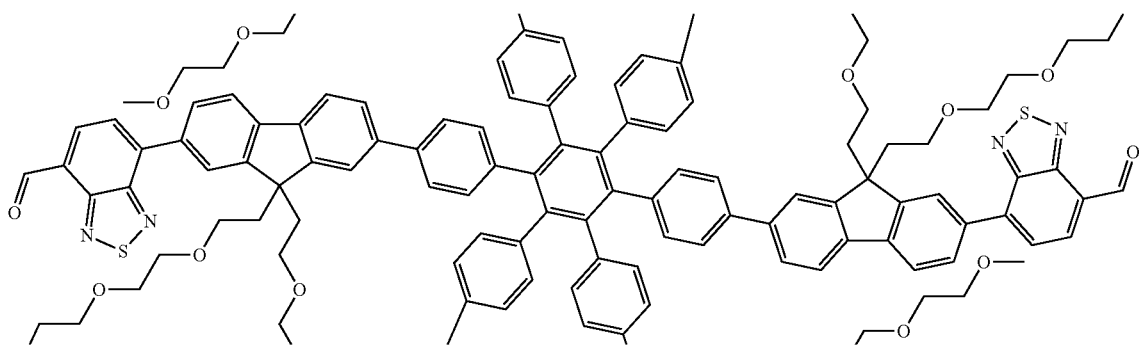

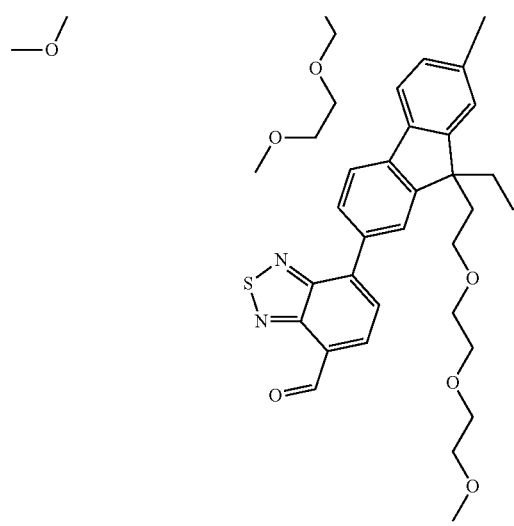
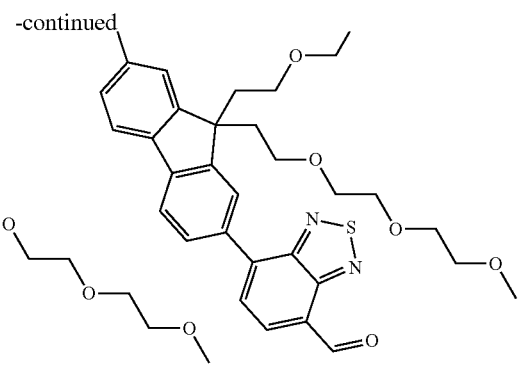

A mixture of WJ06-18 (377 mg, 0.09 mmol), 7-(4,4,5,5-tetramethyl-1,3,2-dioxaborolan-2-yl)benzo[c][1,2,5]thiadiazole-4-carbaldehyde (240 mg, 0.827 mmol), and potassium carbonate (155 mg, 1.12 mmol) in toluene (4 mL), tert-butanol (0.6 mL), and water (0.6 mL) was subjected to three freeze-pump-thaw cycles with backfilling with argon. Tetrakis(triphenylphosphine) palladium (0) (14 mg, 0.01 mmol) was added, and the solution heated in an oil bath held at 60° C. for overnight under argon in the absence of light. The solution was allowed to cool to room temperature and diluted with dichloromethane (50 mL), diethyl ether (200 mL), and water (100 mL). The organic phase was separated, and the aqueous phase was extracted with dichloromethane (3×20 mL). The combined organic extracts were dried over anhydrous sodium sulfate, filtered, and the solvent was removed in vacuo. The crude residue was purified by size exclusion chromatography (Bio-Beads) using tetrahydrofuran as eluent to afford an orange solid after removal of the solvent. The solid was reprecipitated from a mixture of dichloromethane and methanol in an acetone/dry ice bath to give WJ07-20 as a yellow solid (303 mg, 76%). 1H NMR (500 MHZ, (CD$_3$)$_2$SO) δ: 2.32-2.83 (br. m, GIH), 3.08-3.28 (br. m, GIH), 7.16-8.50 (br. m, PhH, FIH and BTH), 10.67-10.69 (br. m, aldehyde H); GPC: $\overline{M}_n$=2654, PDI=1.007.

WJ07-24

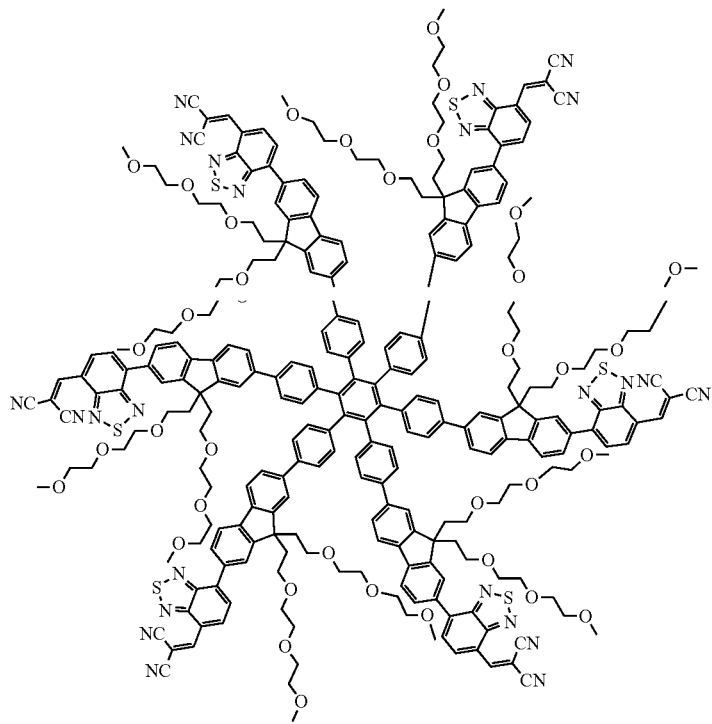

A mixture of WJ07-20 (49.6 mg, 0.012 mmol) and malononitrile (28.8 mg, 0.436 mmol) in chlorobenzene (3 mL) was evacuated and backfilled with argon three times. Pyridine (0.15 mL) was added and the solution heated in an oil bath held at 70° C. for 48 hrs in the absence of light, under a blanket of argon. The solution was allowed to cool to room temperature and the solvent removed in vacuo. The crude was purified by size exclusion chromatography (Bio-Beads) using tetrahydrofuran as eluent followed by reprecipitation from a mixture of dichloromethane and methanol in an acetone/dry ice bath to afford WJ07-24 as a bright red solid (26 mg, 49%). $^1$H NMR (500 MHZ, $(CD_3)_2SO$) δ: 1.95-2.90 (m, GIH), 2.93-3.46 (m, GIH), 6.02-6.13 (m, PhH), 6.74-9.33 (m, PhH and BTH and FIH). GPC: $\overline{M}_n$=3308, PDI=1.055.

Example 2: Testing of the Sensing Materials-Vapour Phase Quenching

Analyte Preparation—Converting the Salts into the Free-Base:

Fentanyl hydrochloride (40.7 mg, 0.109 mmol) was dissolved into aqueous NaOH (0.1 M, 11 mL). Diethyl ether (3 mL) was added and the mixture shaken vigorously several times. The layers were separated, and the aqueous solution extracted with ether (4×2 mL). The combined organic extracts were washed with water (3×2 mL), dried over sodium carbonate, filtered through filter paper, and the solvent removed by blowing with nitrogen until a solid has formed. The solid was then further dried under vacuum (200 mbar) for 30 sec.

Methamphetamine hydrochloride (11.8 mg, 0.063 mmol) was dissolved into aqueous NaOH (0.1 M, 3 mL). Diethyl ether (3 mL) was added and the mixture shaken vigorously several times. The layers were separated, and the aqueous solution extracted with ether (4×2 mL). The combined organic extracts were washed with water (3×2 mL), dried over sodium carbonate, filtered through filter paper, and the solvent removed by blowing with nitrogen for 5 mins. The colourless oil was then further dried under vacuum (200 mbar) for 30 sec.

Cocaine hydrochloride (40.0 mg, 0.118 mmol) was dissolved into aqueous NaOH (0.1 M, 11 mL). Diethyl ether (3 mL) was added and the mixture shaken vigorously several times. The layers were separated, and the aqueous solution extracted with ether (3×2 mL). The combined organic extracts were washed with water (3×2 mL), dried over sodium carbonate, filtered through filter paper, and the solvent removed by blowing with nitrogen for 5 mins. The colourless oil was then further dried under vacuum (200 mbar) for 30 sec.

3,4-Methylenedioxyamphetamine hydrochloride (39.0 mg, 0.181 mmol) was dissolved into aqueous NaOH (0.1 M, 18 mL). Diethyl ether (3 mL) was added and the mixture shaken vigorously several times. The layers were separated, and the aqueous solution extracted with ether (4×2 mL). The combined organic extracts were washed with water (3×2 mL), dried over sodium carbonate, filtered through filter paper, and the solvent removed by blowing with nitrogen for 5 mins. The colourless oil was then further dried under vacuum (200 mbar) for 30 sec.

Film Preparation:

A stock solution of the sensing compound (10 mg/mL concentration) was made by adding 0.10 mL of chloroform (distilled from potassium carbonate) to ~1.0 mg of the sensing compound. The compound was then spin-coated onto quartz substrates (12 mm diameter, 1 mm thickness) using a spin-coater (Specialty Coating Systems, G3P-8, 1600 RPM, 60 sec dwell, 1 sec ramp) to produce thin films of the sensing compound on the substrate.

Analyte Testing:

The films on the substrate were secured onto a film holder inside the detection instrument setup. The film was then excited at 365 nm (Ocean Optics, LSM-365A) and the photoluminescence spectrum from 200 to 800 nm continuously recorded (Ocean Optics, Flame Spectrometer). Specific kinetics of each compound was also continuously recorded (example: sum of the emission from 450-700 nm). A baseline of the photoluminescence was recorded for 20 sec. The film holder (including secured film) was removed and the centre of the film positioned over the mouth of a 20 mL vial containing the target analyte for 20 secs. The film holder was quickly replaced inside the detection instrument and the photoluminescence recorded. This process was repeated three times on three separate films.

Some analytes were required to be heated to achieve a detectable vapour pressure. For example, the synthesised fentanyl free base was equally split into three 20 ml vials. The vials, along with three blank vials were heated in a sand bath at 160° C. The above process was repeated, except the film was first exposed to the heated blank vials in order (to correct for any photoluminescent changes from hot air compared to the analyte) and then to the three analyte vials in order.

Analyte vial temperatures used in the measurements: Methamphetamine free base—room temperature (~22° C.); Fentanyl free base—~160° C.; Cocaine free base—90° C.; 3,4-Methylenedioxyamphetamine free base—30° C. The quenching data for exemplar sensing materials is summarized in Table 1 with examples of the change in fluorescence shown in FIGS. 2a to 2k. In these examples the films are fluorescent in the absence of the analyte. In the presence of the analyte the fluorescence from the films decrease, with the decrease increasing over time as more analyte is absorbed into the films. It should be noted that not all sensing materials detect all narcotic analytes, thus providing a potential route for identification of specific narcotics when a selected combination of sensing materials is used.

TABLE 1

Quenching data for sensing compounds with various analytes

| Sensing Compound (free base) Code | Methamphetamine | Cocaine | MDA | Fentanyl |
|---|---|---|---|---|
| Fl-BT 2.27 | ✓ | | | |
| AL03-77 | ✓ | | | |
| AL03-79 | ✓ | | ✓ | ✓ |
| Fl-BT-Fl 2.16 | | | | ✓ |
| AL03-56 | | | | |
| AL03-28 | | | ✓ | |
| Fl-BTBT-Fl 2.19 | | | | |
| AL03-100 | | | | |
| AL03-102 | | | ✓ | |
| AL03-116 | ✓ | ✓ | ✓ | ✓ |
| AL03-96 | ✓ | ✓ | ✓ | ✓ |
| AL03-35 | ✓ | ✓ | ✓ | ✓ |
| K12 3.4 | ✓ | ✓ | ✓ | ✓ |
| AL-4-09 | ✓ | ✓ | ✓ | ✓ |
| JED | ✓ | ✓ | ✓ | ✓ |
| G1-BT-G1 | ✓ | | | |

TABLE 1-continued

Quenching data for sensing compounds with various analytes

| Sensing Compound (free base) | Code | Methamphetamine | Cocaine | MDA | Fentanyl |
|---|---|---|---|---|---|
| | 2.10 | | | | |
| | G1-BTBT-G1 | | | | |
| | 2.12 | | | | |
| | WJ05-106 | | | | |
| | WJ05-113 | ✓ | | | |
| | K12b | | | ✓ | |
| | 4.20 | | | | |
| | 4.24 | ✓ | | ✓ | |
| | 4.7 | | | | |
| | K12-Th | | | ✓ | |
| | 4.8 | | | | |
| | WJ07-24 | | | ✓ | |

✓: indicates reduction in fluorescence is observed.

Example 3: Testing of the Sensing Materials-Vapour Phase Quenching and Recovery

After measuring the quenching of the fluorescence caused by each of the analytes the sensing films were removed from the analyte source to demonstrate the reversibility of the quenching process. FIGS. 3a to 3g show the initial film luminescence, the decrease in luminescence after 60 seconds exposure to the analyte and the recovery of the luminescence that has occurred after 20 seconds.

Example 4: Testing of Sensing Materials-Solution Phase

Preparation of Film Coating

Sensing compound K12 (4 mg) was dissolved in chloroform (0.4 mL) and the solution was cast on a transparent glass slide (15×40 mm) by spin coating. After the solvent had evaporated, a K12 coating of 50-80 nm thickness remained. The sensing compound JED was cast on a glass substrate using a similar procedure.
Evaluation of Quenching
K12 and Fentanyl Hydrochloride Fentanyl hydrochloride (1.83 mg) was diluted in water (1.0 mL). K12 was deposited on a glass slide by solution casting as described above and was placed in a cuvette filled with water. A 20 µL aliquot of the fentanyl hydrochloride solution was added, and left for 2 minutes before the photoluminescence was recorded. Addition of an aliquot was repeated a further six times.

The results are plotted in the graphs of FIG. 4. FIG. 4a illustrates the change in fluorescence of compound K12 in the presence of an increasing concentration of the analyte, fentanyl hydrochloride, thus demonstrating fluorescence quenching of K12 in the presence of the analyte. FIG. 4b shows the corresponding $PL_0/PL$ values plotted against the concentration of fentanyl hydrochloride demonstrating a quantitative correlation between the degree of quenching of K12 and the concentration of the analyte in the solution being tested.
K12 and MDA Hydrochloride or Cocaine Hydrochloride The above procedure for the evaluation of the quenching effect of fentanyl hydrochloride on the fluorescence of K12 was repeated using analyte solutions comprising MDA hydrochloride (3,4-methylenedioxyamphetamine hydrochloride) or cocaine hydrochloride.

The results are illustrated graphically in FIGS. 5a/b (MDA hydrochloride) and FIGS. 6a/b (cocaine hydrochloride). Both sets of data demonstrate fluorescence quenching of K12 in the presence of the analyte (FIGS. 5a and 6a). FIGS. 5b and 6b also demonstrate a quantitative correlation between the degree of quenching of K12 and the concentration of the analyte in the solution being tested.

The invention claimed is:

1. An optical sensing element for detection of a narcotic, the optical sensing element comprising a fluorescent sensing compound provided on a substrate, wherein emission of the fluorescent sensing compound is quenched in the presence of the narcotic, and wherein the fluorescent sensing compound is non-polymeric and is represented by general formula (IA):

$$A_a B_b C_c D_d E_e \quad (IA)$$

in which:
A comprises one or more of fluorenyl, bisfluorenyl, phenyl, thiophenyl, and terphenyl;
B is an electron acceptor moiety;
C is a moiety that influences solubility of the compound in a solvent;
D is a modifier moiety that enables fine tuning of the optoelectronic properties of the sensing compound;
E is a branching moiety;
a is an integer of 1 or more;
b is an integer of 1 or more;
c is an integer of 1 or more;
d is an integer of 0 to less than or equal to b; and
e is 0 or 1.

2. The optical sensing element of claim 1, wherein the fluorescent sensing compound comprises:

| Fluorescent Sensing Compound (free base) | Code |
|---|---|
|  | AL03-116 |
| | AL03-96 |
| | AL03-35 |
| | K123.4 |

-continued

| Fluorescent Sensing Compound (free base) | Code |
|---|---|
|  | AL-4-09 |
|  | JED | or an acid addition salt thereof.

3. The optical sensing element according to claim 1, wherein the element is for vapour phase detection.

4. The optical sensing element according to claim 1, wherein the element is for solution phase detection.

5. The optical sensing element according to claim 1, wherein the emission of the fluorescent sensing compound is increased when the narcotic is removed.

6. A method for detection of a narcotic in a sample, which method comprises: (a) irradiating an optical sensing element as defined in claim 1 thereby causing fluorescent emission by the fluorescent sensing compound; (b) contacting the sample with the optical sensing element; (c) measuring the luminescence of the fluorescent optical sensing element after contacting with the sample; and (d) determining whether the narcotic is present in the sample based on the measurement obtained in step (c).

7. A sensing device for detection of a narcotic in a sample, the sensing device comprising:
   an optical sensing element as defined in claim 1;
   an irradiation source for irradiating the optical sensing element with stimulating radiation;
   a detector for measuring luminescence of the optical sensing element; and
   means for delivering the sample for contacting with the optical sensing element.

8. An optical sensing element for detection of a narcotic, the optical sensing element comprising a fluorescent sensing compound provided on a substrate, wherein emission of the fluorescent sensing compound is quenched in the presence of the narcotic, and wherein the fluorescent sensing compound is non-polymeric and is represented by general formula (IA):

$$A_aB_bC_cD_dE_e \quad (IA)$$

in which:
A is an electron donor moiety;
B comprises one or more of benzothiadiazolyl, benzoxadiazolyl, oxazolyl, triazinyl, imidazolyl, pyridinyl and quinoxalinyl;
C is a moiety that influences solubility of the compound in a solvent;
D is a modifier moiety that enables fine tuning of the optoelectronic properties of the sensing compound;
E is a branching moiety;
a is an integer of 1 or more;
b is an integer of 1 or more;
c is an integer of 1 or more;
d is an integer of 0 to less than or equal to b; and
e is 0 or 1.

9. The optical sensing element according to claim 8, wherein the element is for vapour phase detection.

10. The optical sensing element according to claim 8, wherein the element is for solution phase detection.

11. The optical sensing element according to claim 8, wherein the emission of the fluorescent sensing compound is increased when the narcotic is removed.

12. A method for detection of a narcotic in a sample, which method comprises: (a) irradiating an optical sensing element as defined in claim 8 thereby causing fluorescent emission by the fluorescent sensing compound; (b) contacting the sample with the optical sensing element; (c) measuring the luminescence of the fluorescent optical sensing element after contacting with the sample; and (d) determining whether the narcotic is present in the sample based on the measurement obtained in step (c).

13. A sensing device for detection of a narcotic in a sample, the sensing device comprising:
   an optical sensing element as defined in claim 8;
   an irradiation source for irradiating the optical sensing element with stimulating radiation;
   a detector for measuring luminescence of the optical sensing element; and
   means for delivering the sample for contacting with the optical sensing element.

14. An optical sensing element for detection of a narcotic, the optical sensing element comprising a fluorescent sensing compound provided on a substrate, wherein emission of the fluorescent sensing compound is quenched in the presence of the narcotic, and wherein the fluorescent sensing compound is non-polymeric and is represented by general formula (IA):

$$A_aB_bC_cD_dE_e \quad (IA)$$

in which:
A is an electron donor moiety;
B is an electron acceptor moiety;
C is a moiety that influences solubility of the compound in a solvent;
D comprises one or more of Rhodanine, a vinyl cyano ester, and a vinyl dicyano vinyl diester;
E is a branching moiety;
a is an integer of 1 or more;
b is an integer of 1 or more;
c is an integer of 1 or more;
d is an integer of 0 to less than or equal to b; and
e is 0 or 1.

15. The optical sensing element according to claim 14, wherein the element is for vapour phase detection.

16. The optical sensing element according to claim 14, wherein the element is for solution phase detection.

17. The optical sensing element according to claim 14, wherein the emission of the fluorescent sensing compound is increased when the narcotic is removed.

18. A method for detection of a narcotic in a sample, which method comprises: (a) irradiating an optical sensing element as defined in claim 14 thereby causing fluorescent emission by the fluorescent sensing compound; (b) contacting the sample with the optical sensing element; (c) measuring the luminescence of the fluorescent optical sensing element after contacting with the sample; and (d) determining whether the narcotic is present in the sample based on the measurement obtained in step (c).

19. A sensing device for detection of a narcotic in a sample, the sensing device comprising:

an optical sensing element as defined in claim 14;
an irradiation source for irradiating the optical sensing element with stimulating radiation;
a detector for measuring luminescence of the optical sensing element; and
means for delivering the sample for contacting with the optical sensing element.

\* \* \* \* \*